US008389244B2

(12) United States Patent
Rossi et al.

(10) Patent No.: US 8,389,244 B2
(45) Date of Patent: Mar. 5, 2013

(54) METHODS AND KITS FOR SYNTHESIS OF SIRNA EXPRESSION CASSETTES

(75) Inventors: John J. Rossi, Alta Loma, CA (US); Daniela Castanotto, Altadena, CA (US)

(73) Assignee: City of Hope, Duarte, CA (US)

( * ) Notice: Subject to any disclaimer, the term of this patent is extended or adjusted under 35 U.S.C. 154(b) by 721 days.

(21) Appl. No.: 10/630,968

(22) Filed: Jul. 31, 2003

(65) Prior Publication Data
US 2004/0091918 A1 May 13, 2004

Related U.S. Application Data

(60) Provisional application No. 60/399,718, filed on Aug. 1, 2002, provisional application No. 60/408,298, filed on Sep. 6, 2002.

(51) Int. Cl.
C12P 19/34 (2006.01)
C12Q 1/68 (2006.01)
C12N 5/00 (2006.01)
C12N 5/02 (2006.01)
C12N 15/11 (2006.01)
C07H 21/02 (2006.01)
C07H 21/04 (2006.01)

(52) U.S. Cl. .... 435/91.1; 435/6.1; 435/91.2; 435/91.21; 435/325; 435/375; 536/23.1; 536/24.5; 514/44 A

(58) Field of Classification Search .................. 514/44, 514/679; 435/4, 6, 325, 375, 455, 5; 536/23.1, 536/24.5; 424/93.21
See application file for complete search history.

(56) References Cited

U.S. PATENT DOCUMENTS

| | | | |
|---|---|---|---|
| 5,624,803 A * | 4/1997 | Noonberg et al. | 435/6 |
| 5,795,715 A | 8/1998 | Livache et al. | |
| 5,814,500 A * | 9/1998 | Dietz | 435/455 |
| 5,869,249 A | 2/1999 | Rossi | |
| 5,958,738 A * | 9/1999 | Lindemann et al. | 435/91.2 |
| 6,100,087 A | 8/2000 | Rossi et al. | |
| 6,506,559 B1 | 1/2003 | Fire et al. | |
| 2003/0059944 A1 * | 3/2003 | Lois-Caballe et al. | 435/456 |
| 2003/0148519 A1 * | 8/2003 | Engelke et al. | 435/455 |
| 2003/0149113 A1 * | 8/2003 | Caplan et al. | 514/679 |
| 2003/0180756 A1 * | 9/2003 | Shi et al. | 435/6 |
| 2004/0001811 A1 * | 1/2004 | Kreutzer et al. | 424/93.21 |

OTHER PUBLICATIONS

Jeng et al., Transcription Termination by Bacteriophage T7 RNA Polymerase at Rho-independent Terminators, Mar. 1990, JBC, vol. 265, No. 7, pp. 3823-3830.*
Thomas Tuschl, Expanding small RNA interference, May 2002, Nature Biotechnology, vol. 20, pp. 446-448.*
Jones et al., DNA mutagenesis and recombination, Apr. 1990, Nature, vol. 344, pp. 793-794.*
Paddison et al., Short hairpin RNAs induce sequence-specific silencing in mammalian cells, Apr. 2002, Genes & Development, vol. 16, pp. 948-958.*
Gou et al., Gene silencing in mammalian cells by PCR-based short hairpin RNA., First published online Jul. 4, 2003, FEBS, vol. 548, pp. 113-118.*
Castanotto et al., Functional siRNA expression from transfected PCR products., 2002., RNA, vol. 8, pp. 1454-1460.*
Bryan R. Cullen, RNA interference: antiviral defense and genetic tool, Jul. 2002, Nature Immunology, vol. 3, pp. 597-599.*
Kennerdell et al., Heritable gene silencing in *Drosophila* using double-stranded RNA, Jul. 2000, Nature Biotechnology, vol. 17, pp. 896-898.*
Tuschl et al., Small Interfering RNAs: A revolutionary tool for the anaylsis of gene function and gene therapy., Molecular Interventions, Jun. 2002, vol. 2, pp. 158-167.*
Medina et al., Design, characterization and testing of tRNA3lys-based hammerhead ribozymes, 1999, Nucleic Acids Research, vol. 27, pp. 1698-1708.*
Lee et al., Expression of small interfering RNAs targeted against HIV-1 rev transcripts in human cells, 2002, Nature Biotechnology, vol. 19, pp. 500-506.*
MacFerrin et al., Overproduction and dissection of proteins by the expression-cassette polymerase chain reaction, 1990, PNAS, vol. 87, pp. 1937-1941.*
Stoflet et al., 1988, Science, vol. 239, pp. 491-494.*
Bertrand, Edouard, et al., "The expression cassette determines the functional activity of ribozymes in mammalian cells by controlling their intracellular localization," *RNA* 3:75-88, 1997.
Brummelkamp, Thijn R., et al., "A System for Stable Expression of Short Interfering RNAs in Mammalian Cells," *Science* 296:550-553, Apr. 19, 2002.
Cagnon, Laurence, et al., "Downregulation of the CCR5 β-Chemokine Receptor and Inhibition of HIV-1 Infection by Stable VA1-Ribozyme Chimeric Transcripts," *Antisense & Nucleic Acid Drug Development* 10:251-261, 2000.
Elbashir, Sayda M., et al., "Duplexes of 21-nucleotide RNAs mediate RNA interference in cultured mammalian cells," *Nature* 411:494-498, May 24, 2001.
Good, P.D., et al., "Expression of small, therapeutic RNAs in human cell nuclei," *Gene Therapy* 4:45-54, 1997.
Paul, Cynthia P., et al., "Effective expression of small interfering RNA in human cells," *Nature Biotechnology* 29:505-508, May 2002.
Yu, Jenn-Yah, et al., "RNA interference by expression of short-interfering RNAs and hairpin RNAs in mammalian cells," *PNAS* 99(9):6047-6052, Apr. 30, 2002.
Sharp, Phillip A., et al., "RNA interference—2001," *Genes & Development* 15:485-490, 2001.
Lee, Nan Sook, et al., "Functional colocalization of ribozymes and target mRNAs in *Drosophila* oocytes," *The FASEB Journal* 15:2390-2400, Nov. 2001.
Barton, Gregory M., et al., "Retroviral delivery of small interfering RNA into primary cells," *PNAS* 99(23):14943-14945, Nov. 12, 2002.

(Continued)

Primary Examiner — Dana Shin
(74) Attorney, Agent, or Firm — Rothwell, Figg, Ernst & Manbeck p.c.

(57) ABSTRACT

Amplification-based methods and kits for rapidly producing siRNA expression cassettes are provided. Also provided are methods for expressing amplified siRNA expression cassettes in cells.

20 Claims, 9 Drawing Sheets

OTHER PUBLICATIONS

Caplen, Natasha J., et at, "Specific inhibition of gene expression by small double-stranded RNAs in invertebrate and vertebrate systems," *PNAS* 98(17):9742-9747, Aug. 14, 2001.

Clemens, James C., et al., "Use of double-stranded RNA interference in *Drosophila* cell lines to dissect signal transduction pathways," *PNAS* 97(12):6499-6503, Jun. 6, 2000.

Devroe, Eric, et al., "Retrovirus-delivered siRNA," *BMC Biotechnology* 2(15):1-5, Aug. 28, 2002.

Elbashir, Sayda M., et al., "RNA interference is mediated by 21- and 22-nucleotide RNAs," *Genes & Development* 15:188-200, 2001.

Fire, Andrew, "RNA-triggered gene silencing," TIG 15(9):358-363, Sep. 1999.

Fire, Andrew, "Potent and specific genetic interference by double-stranded RNA in *Caenorhabditis elegans*," *Nature* 391:806-811, Feb. 19, 1998.

Hammond, Scott M., et al., "An RNA-directed nuclease mediates post-transcriptional gene silencing in *Drosophila* cells," *Nature* 404:293-296, Mar. 16, 2000.

Lipardi, Concetta, et al., "RNAi as Random Degradative PCR: siRNA Primers Convert mRNA into dsRNAs that are Degraded to Generate New siRNAs," *Cell* 107:297-307, Nov. 2, 2001.

Sijen, Titia, et al., "On the Role of RNA Amplification in dsRNA-Triggered Gene Silencing," *Cell* 107:465-476, Nov. 16, 2001.

Wianny, Florence, et al., "Specific interference with gene function by double-stranded RNA in early mouse development," *Nature Cell Biology* 2:70-75, Feb. 2000.

Liu, W.M., et al., "Proposed roles for DNA methylation in *Alu* transcriptional repression and mutational inactivation", Nucleic Acids Research, vol. 21, No. 6, 1993, pp. 1351-1359.

\* cited by examiner

METHODS AND KITS FOR SYNTHESIS OF SIRNA EXPRESSION CASSETTES

This application claims priority to U.S. Provisional Application Ser. Nos. 60/399,718 filed Aug. 1, 2002 and 60/408,298 filed Sep. 6, 2002.

GOVERNMENT RIGHTS STATEMENT

This invention was made with federal government support from the National Institutes of Health of the U.S. Department of Health and Human Services under Grant No. AI29329 to the City of Hope Cancer Center. The United States government may have certain rights in this invention.

FIELD OF THE INVENTION

The present invention relates to RNA interference (RNAi), and is useful for screening multiple RNAi gene constructs to identify those most effective against a given target.

BACKGROUND OF THE INVENTION

RNA interference (RNAi) is a process in which double stranded RNA (ds RNA) induces the postranscriptional degradation of homologous transcripts, and has been observed in a variety of organisms including plants, fungi, insects, protozans, and mammals. (Moss, E. G., et al., 2001; Bernstein, E., et al., 2001; Elbashir, S. M., et al., 2001; Elbashir, S. M., et al., 2001). RNAi is initiated by exposing cells to dsRNA either via transfection or endogenous expression. Double-stranded RNAs are processed into 21 to 23 nucleotide (nt) fragments known as siRNA (small interfering RNAs). (Elbashir, S. M., et al., 2001; Elbashir, S. M., et al., 2001). These siRNAs form a complex known as the RNA Induced Silencing Complex or RISC (Bernstein, E., et al., Hammond, S. M., et al. 2001), which functions in homologous target RNA destruction. In mammalian systems, the sequence specific RNAi effect can be observed by introduction of siRNAs either via transfection or endogenous expression of 21-23 base transcripts or longer hairpin precursors. Use of siRNAs evades the dsRNA induced interferon and PKR pathways that lead to non-specific inhibition of gene expression. (Elbashir, S. M., et al., 2001).

Recently, several groups have demonstrated that siRNAs can be effectively transcribed by Pol III promoters in human cells and elicit target specific mRNA degradation. (Lee, N. S., et al., 2002; Miyagishi, M., et al., 2002; Paul, C. P., et al., 2002; Brummelkamp, T. R., et al., 2002; Ketting, R. F., et al., 2001). These siRNA encoding genes have been transiently transfected into human cells using plasmid or episomal viral backbones for delivery. Transient siRNA expression can be useful for rapid phenotypic determinations preliminary to making constructs designed to obtain long term siRNA expression. Of particular interest is the fact that not all sites along a given mRNA are equally sensitive to siRNA mediated downregulation. (Elbashir, S. M., et al., 2001; Lee, N. S., et al., 2001; Yu, J. Y., et al., 2002; Holen, T, et al., 2002).

In contrast to post-transcriptional silencing involving degradation of mRNA by short siRNAs, the use of long siRNAs to methylate DNA has been shown to provide an alternate means of gene silencing in plants. (Hamilton, et al.). In higher order eukaryotes, DNA is methylated at cytosines located 5' to guanosine in the CpG dinucleotide. This modification has important regulatory effects on gene expression, especially when involving CpG-rich areas known as CpG islands, located in the promoter regions of many genes. While almost all gene-associated islands are protected from methylation on autosomal chromosomes, extensive methylation of CpG islands has been associated with transcriptional inactivation of selected imprinted genes and genes on the inactive X-chromosomes of females. Aberrant methylation of normally unmethylated CpG islands has been documented as a relatively frequent event in immortalized and transformed cells and has been associated with transcriptional inactivation of defined tumor suppressor genes in human cancers. In this last situation, promoter region hypermethylation stands as an alternative to coding region mutations in eliminating tumor suppression gene function. (Herman, et al.). The use of siRNAs for directing methylation of a target gene is described in U.S. Provisional Application No. 60/447,013, filed Feb. 13, 2003, which is incorporated herein by reference.

There are at this time no rules governing siRNA target site selection for a given mRNA target. It is therefore important to be able to rapidly screen potential target sequences to identify a sequence or sequences susceptible to siRNA mediated degradation. Initial attempts at addressing this problem have taken advantage of an oligonucleotide/RNAseH procedure in cell extracts on native mRNA transcripts designed to identify sites that are accessible to base-paring, including pairing by nucleic acid products such as ribozymes. This approach has also been applied to identifying binding sites for siRNA (Lee, N. S. et al. 2001). Having identified an accessible site with the oligonucleotide/RNAseH procedure it is still necessary to generate siRNAs against the target at the accessible site. This approach has been applied to siRNA site accessibility as well. (Lee, N. S., et al., 2001). However, this process can be time consuming, and in the end it is still necessary to synthesize the siRNA genes for final testing.

Thus, an object of the present invention is to provide an amplification-based approach in the form of a method and kit for rapidly synthesizing siRNA genes, so as to permit rapid screening of potential target sequences susceptible to siRNA mediated degradation.

Another object of the invention is to provide a method for controlling or inhibiting expression of a target gene by transfecting a cell with an amplified siRNA expression cassette.

SUMMARY OF THE INVENTION

The present invention provides an amplification-based approach (e.g., Polymerase Chain Reaction (PCR)) for rapid synthesis of promoter-containing siRNA expression cassettes, and their subsequent transfection into cells. This approach, which includes methods and kits for performing the methods, can be utilized for the facile screening of siRNA encoding genes to identify those encoding siRNAs having the best functional activity for a given target. The approach can be utilized with siRNAs expressed independently from promoters or with siRNAs expressed as hairpin precursors or other precursors. The amplification products produced using the approach may be used directly, without subsequent cloning, by transfecting them into cells followed by functional assays.

The method of the present invention is fast and inexpensive, allowing multiple different siRNA gene candidates and/or promoter candidates to be rapidly screened for efficacy before cloning into a vector.

The method of the present invention is useful for screening siRNA gene libraries.

DETAILED DESCRIPTION OF THE INVENTION

Figure 1:
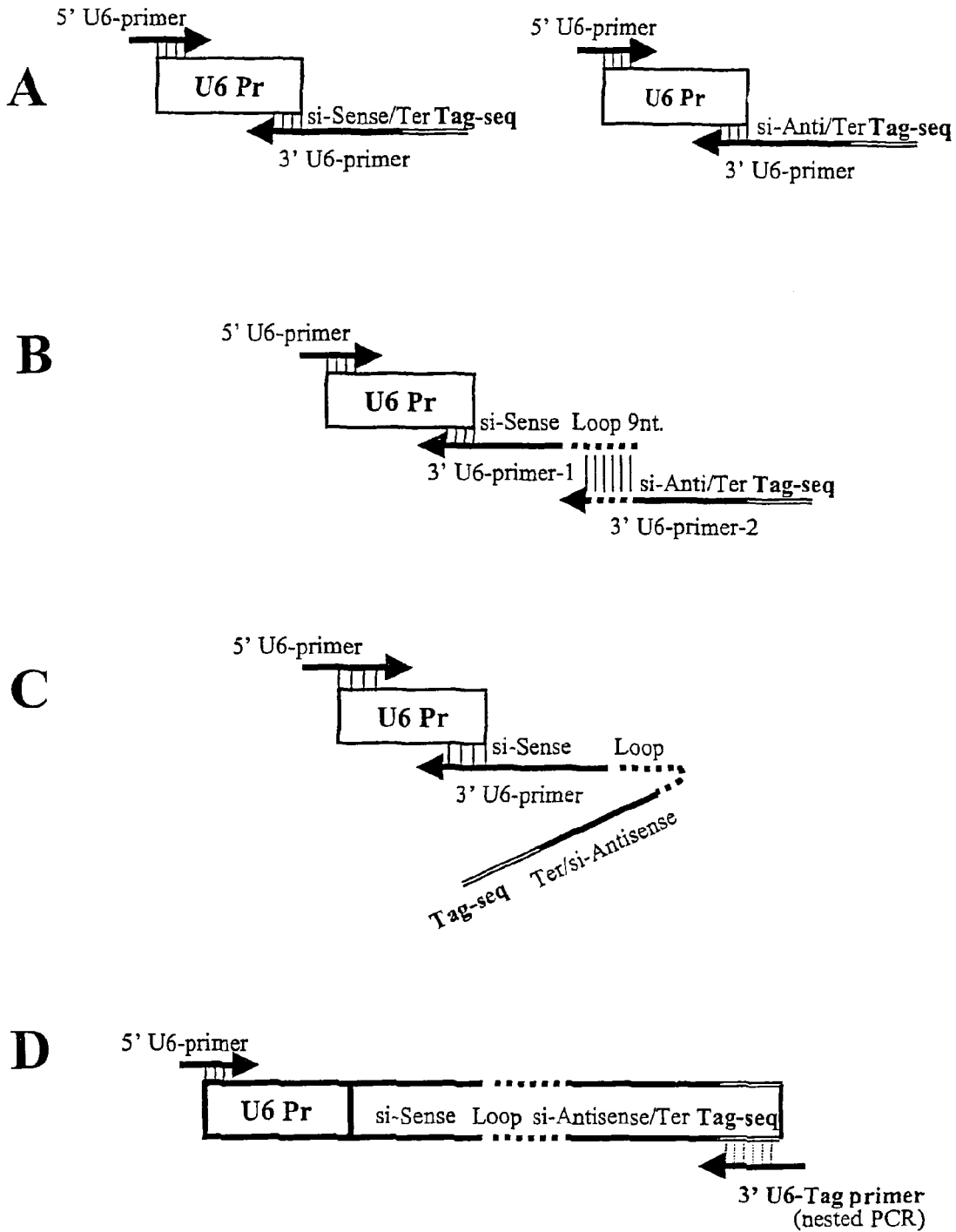
FIG. 1 is a schematic representation of a PCR strategy used to yield U6 transcription cassettes expressing siRNAs. The 5' PCR primer is complementary to the 5' end of the U6 promoter and is standard for all PCR reactions. A) The 3' PCR primer is complementary to sequences at the 3' end of the U6 promoter and is followed by either the sense or antisense sequences, a stretch of four to six deoxyadenosines (Ter) and an additional "stuffer-Tag" sequence. The adenosines are the termination signal for the U6 Pol III promoter; therefore, any sequence added after this signal will not be transcribed by the Pol III polymerase and will not be part of the siRNA. B) The sense and antisense sequences are linked by a 9 nt loop and are inserted in the cassette by a two-step PCR reaction. C) The sense and antisense sequences linked by a 9-nucleotide loop and followed by the stretch of adenosines and by the Tag sequences are included in a single 3' primer. D) Complete PCR expression cassette obtained by the PCR reaction. To amplify and identify functional siRNAs from the transfected cells, or to increase the yield of the PCR product shown in D, a nested PCR can be performed using the universal 5' U6 primer and a 3' primer complementary to the Tag sequence (also standard), as indicated in the figure.

The present invention provides an amplification-based method for producing a promoter-containing siRNA expression cassette.

In one embodiment, the method comprises:
i) treating one strand of a double-stranded promoter sequence or construct, in an amplification reaction mixture, with an oligonucleotide primer which is complementary to the 5' end of the promoter sequence;
ii) treating the other strand of the promoter sequence or construct, in the amplification reaction mixture, with a second oligonucleotide primer which is complementary to the 3' end of the promoter sequence, wherein the second primer comprises one or more sequences which are complementary to a sequence encoding a sense or (and/or) antisense sequence of a siRNA molecule, optionally along with one or both of a loop sequence and a terminator sequence; and
iii) treating the amplification reaction mixture of steps (i) and (ii) in an amplification reaction at a temperature for annealing and extending said primers on the promoter sequence or construct and at a temperature for denaturing the extension products to provide an amplified product comprising the promoter, one or more sequences encoding the sense or (and/or) antisense sequence of the siRNA, and one or both of the loop sequence and the terminator sequence.

The steps (i)-(iii) can be repeated a sufficient number of times to amplify and detect the promoter-containing siRNA expression cassette. It is also recognized that alternatives to the loop sequence and/or terminator sequence may be utilized in the invention, which are capable of achieving the same function or purpose as the loop and terminator sequences. It is also recognized that variations in the above steps are encompassed within the invention, in the event these variations also provide an amplification-based method for producing a promoter-containing siRNA expression cassette. It is further recognized that the term complementary, although in a preferred embodiment refers to a perfect base-paired match between two sequences, may not require such, and thus the term complementary also encompasses those sequences not having a perfect base-paired match but which are otherwise able to achieve the intended result of the invention.

The terms "loop sequence" and "terminator sequence" refer to the sequences corresponding to the loop and terminator elements, including the final sequences and any precursor sequences such as the sequences encoding the final sequences, and any complementary sequences.

In a preferred embodiment, the method is a PCR-based method. However, it is recognized that the invention may be practiced based on other amplification methods known currently or in the future.

The promoter may be any promoter capable of transcribing an siRNA molecule, and is preferably one that can transcribe siRNA in mammalian cells. In a preferred embodiment, the promoter is a Pol III promoter, more preferably a mammalian U6 promoter, and most preferably a human U6 promoter. Other promoters, such as the H1 promoter, U1 or tRNA promoters such as tRNA Val, Met or Lys3 may also be useful in the present invention. It is also possible to use Pol II promoters such as the U1 snRNA promoter.

The terminator sequence may be any sequence encoding a functional terminator sequence. In a preferred embodiment, the terminator sequence comprises a sequence of deoxyadenosines, preferably about 4-6 deoxyadenosines, and more preferably a sequence of 6 deoxyadenosines.

In another embodiment, the second primer may further comprise a tag sequence to identify functional siRNA encoding sequences. In a more preferred embodiment, the tag sequence may further comprise a restriction site useful for cloning.

In one embodiment, the second primer comprises a sequence that is complementary to a sequence encoding a sense sequence, along with a terminator sequence or loop sequence.

In another embodiment, the second primer comprises a sequence that is complementary to a sequence encoding an antisense sequence, along with a terminator sequence or loop sequence.

In still another embodiment, the second primer comprises a sequence that is complementary to a sequence encoding a sense sequence and a sequence that is complementary to a sequence encoding an antisense sequence of said siRNA molecule, along with a terminator sequence.

In a preferred embodiment of the above embodiment, the sense and antisense sequences may be attached by a loop sequence. The loop sequence may comprise any sequence or length that allows expression of a functional siRNA expression cassette in accordance with the invention. In a preferred embodiment, the loop sequence contains higher amounts of uridines and guanines than other nucleotide bases. The preferred length of the loop sequence is about 4 to about 9 nucleotide bases, and most preferably about 8 or 9 nucleotide bases.

The amplified products of the present method will vary depending on which embodiment above is selected.

The sequences or constructs encoding the sense and antisense sequences preferably contain about 19-29 nucleotides, more preferably about 19-23 nucleotides, and most preferably about 21 nucleotides. The siRNA molecules also may contain 3' nucleotide, preferably 3' dinucleotide overhangs, including 3'UU. More generally, the RNAi or siRNA molecules also include those known in the art.

In one embodiment, the amplified product comprises the promoter and a sequence or construct encoding either the sense or antisense sequence of the siRNA molecule. The amplified product also may contain the loop sequence or the terminator sequence.

In another embodiment, the amplified product comprises the promoter, a sequence or construct encoding either the sense or antisense sequence of the siRNA molecule, and the terminator sequence.

In another embodiment, the amplified product comprises the promoter, a sequence or construct encoding either the sense or antisense sequence of the siRNA molecule, and the loop sequence. In this embodiment, the amplified product may be treated in another amplification reaction to provide another amplified product. This may be achieved using a third oligonucleotide primer. A portion of this third primer is complementary to the loop sequence of the first amplified product. The third primer also comprises a sequence complementary to a sequence encoding the antisense sequence when the first amplified product contains the sense encoding sequence, or a sequence complementary to a sequence encoding the sense sequence when the first amplified product contains the antisense encoding sequence. The third primer also may include a terminator sequence.

In another embodiment, the amplified product comprises the promoter, a sequence or construct encoding the sense sequence and a sequence or construct encoding the antisense sequence of the siRNA molecule. In this embodiment, the sense and antisense encoding sequences or constructs may be attached by a loop sequence. The amplified product also may contain a terminator sequence.

In still another embodiment, amplified products are produced that comprise the promoter, a sequence or construct encoding the sense sequence and a sequence or construct encoding the antisense sequence of the siRNA molecule. The sense and antisense encoding sequences or constructs may be attached by a loop sequence. The amplified products also may contain a terminator sequence.

In yet another embodiment, the amplified product, in another amplification reaction, can be treated with a fourth oligonucleotide primer, a portion of which is complementary with the tag sequence.

In a preferred embodiment, the method may further comprise the step of purifying the amplified promoter-containing siRNA expression cassette. Various purification techniques are known in the art and may be used in the present invention. Examples are described below.

In another embodiment, the amplified, and preferably purified, promoter-containing siRNA expression cassette produced according to the invention is transfected into cells for screening. After transfection, the siRNA can be expressed to induce gene silencing.

Figure 9:
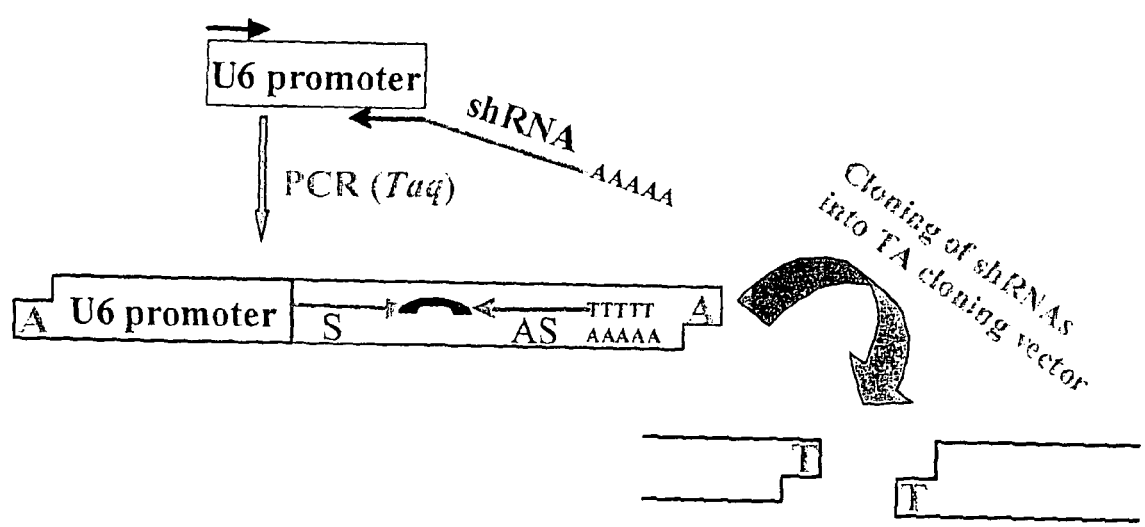
FIG. 9 shows schematically an embodiment of the present invention in which a PCR-amplified siRNA expression cassette is cloned into a cloning vector.

In another embodiment, a selected and preferably purified, promoter-containing siRNA expression cassette is cloned into a selected vector. For this embodiment, it is recognized that restriction sites can be inserted at the ends of the siRNA expression cassette, preferably during production, for example, by including restriction site-encoding sequences within the primers. A schematic of this embodiment is shown in FIG. 9, as well as in U.S. Provisional Application No. 60/399,397, filed Jul. 31, 2002, which is incorporated herein by reference.

In a preferred embodiment, the selected cells are mammalian cells.

In another preferred embodiment, one or more of the oligonucleotide primers are modified, preferably by phosphorylation.

In another embodiment, the method also comprises the step of screening for a target site on mRNA sensitive to the expressed siRNA molecule.

In another embodiment, the method includes a positive and/or negative control, such as a control cassette.

In another aspect, the invention provides a method for inhibiting expression of a target gene. The method comprises transfecting a cell with an amplified, and preferably purified, siRNA expression cassette so that a siRNA can be expressed and inhibit the target gene. In a preferred embodiment, the cell is transfected with two or more different siRNA expression cassettes. In one embodiment, the different siRNA expression cassettes contain different siRNA encoding genes, including different loop sequences, and/or different promoters.

In another aspect, the invention provides a method for modifying gene function in mammals, for example by directing methylation of a target gene, including a promoter region of the gene, by transfecting a cell with an amplified siRNA expression cassette in accordance with the invention.

In another aspect, the invention provides a PCR-based approach in the form of a kit for producing a promoter-containing siRNA expression cassette. The kit comprises a double-stranded, promoter-containing template, an oligonucleotide primer complementary to the 5' end of the promoter-containing template, and an oligonucleotide primer complementary to the 3' end of the promoter-containing template. The 3' primer also comprises one or more sequences complementary to a sequence encoding a sense or (and/or) antisense sequence of a siRNA molecule.

The 3' primer may further comprise a loop sequence, in which case the kit further comprises an oligonucleotide primer complementary to the loop sequence, which primer comprises a sequence complementary to a sequence encoding a sense or antisense sequence of the siRNA molecule.

In one embodiment, the kit comprises a 3' primer comprising a sequence complementary to a sequence encoding a sense sequence and another 3' primer comprising a sequence complementary to a sequence encoding an antisense sequence.

In another embodiment, the 3' primer comprises a sequence that is complementary to a sequence encoding a sense sequence, a sequence that is complementary to a sequence encoding an antisense sequence, and a terminator sequence. The sequences complementary to the sense and antisense encoding sequences preferably are attached by a loop sequence.

In a preferred embodiment, the oligonucleotide primers are modified, preferably by phosphorylation.

The kit also may comprise PCR amplification reagents and reagents for purifying the amplified siRNA expression cassette.

In another preferred embodiment, the kit also comprises one or both of a positive and negative control.

Preferred embodiments of the invention are described below; however, the invention is understood not to be limited to the following embodiments.

PCR Amplification, Transfection, and Expression of siRNAs in Mammalian Cells.

The procedure for a PCR-based approach is depicted schematically in FIG. 1. In a preferred embodiment, universal primer that is complementary to the 5' end of the human U6 promoter is used in a PCR reaction along with a primer(s) complementary to the 3' end of the promoter, which primer harbors appended sequences which are complementary to the sense or antisense siRNA genes (FIG. 1A). The sense or antisense sequences are followed by a transcription terminator sequence (Ter), which is preferably a stretch of about 4-6 deoxyadenosines, and more preferably a stretch of 6 deoxyadenosines, and by a short additional "stuffer-tag" sequence that may include a restriction site for possible cloning at a later stage. The resulting PCR products include the U6 promoter sequence, the siRNA sense or antisense encoding sequence, a terminator sequence, and a short tag sequence at the 3' terminus of the product.

In another embodiment, both the sense and antisense sequences can be included in the same cassette (FIG. 1B, 1D). In this case a nucleotide loop, preferably containing 9 nucleotides, is inserted between the sense and antisense siRNA sequences. The resulting single PCR product includes the U6 promoter, the siRNA sense and antisense encoding sequences in the form of a stem-loop, the Pol III terminator sequence, and the "stuffer" tag sequence (FIG. 1D). To construct this cassette two 3' primers are used. The first PCR reaction employs the 5' U6 universal primer and a 3' primer complementary to 20 nucleotides of the U6 promoter, followed by sequences complementary to the siRNA sense encoding sequence and the 9 nt. loop (FIG. 1B). One microliter of this first reaction is reamplified in a second PCR reaction that employs the same 5' U6 primer and a 3' primer harboring sequences complementary to the 9 nt. loop appended to the antisense strand, Ter and "stuffer" tag sequence (FIG. 1B).

In another embodiment, a one step PCR reaction is conducted with a single 3' primer that harbors the sense, loop, antisense, Ter and "stuffer' tag sequences (FIG. 1C). Although generally effective, this approach employs a considerably long and structured 3' PCR primer that with some sequences may cause difficulties in obtaining the desired full length, double stranded PCR products.

PCR conditions are relatively standard for all siRNA genes since the regions complementary to the U6 promoter do not change. For the construction of several cassettes, optimal amplification was achieved in each case using 1 minute for each PCR step and 55° C. as annealing temperature. For direct transfections and testing of the PCR amplified siRNA genes, the 5' termini of the PCR primers may be modified, for example, by phosphorylation, preferably using a DNA polynucleotide kinase and non-radioactive ATP. This modification of the primers stabilizes the PCR products intracellularly, thereby enhancing the efficacy of the PCR products.

Once the PCR reaction is completed, the products can be column purified from the primers, e.g., via a gel filtration column or by excising them directly from a gel following electrophoresis. The purified products can be applied to cells following cationic liposome encapsidation and/or standard transfection procedures, such as those described below and in co-pending Application Ser. No. 60/356,127, filed on Feb. 14, 2002, which is incorporated herein by reference. Intracellular expression of the transfected PCR products was detected by Northern blotting analyses (FIG. 3A), thus demonstrating good transfection efficiency.

Rapid Screening of Functional siRNAs and Accessible Target Sites Using siRNA-Encoding PCR Products.

Figure 3:
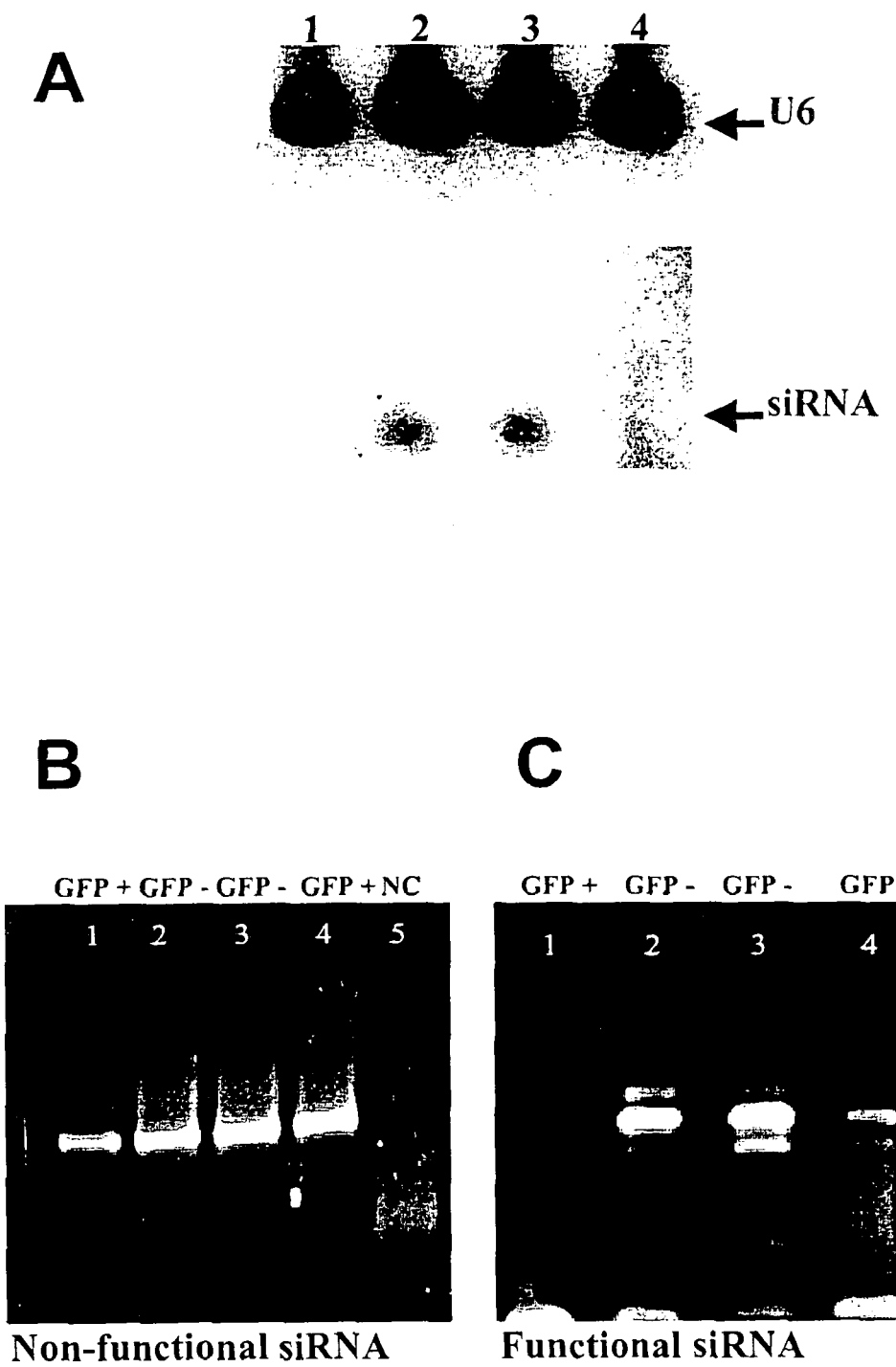
FIG. 3 shows the detection of siRNAs and PCR amplification of siRNA encoding DNAs in transfected cells. A. Northern gel analyses of siRNAs expressed from PCR products transfected in A293 cells. Lane 1, cells transfected with the EFGP target construct alone; Lane 2, cells transfected with antisense encoding construct alone; Lane 3, cells co-transfected with antisense and sense encoding constructs; Lane 4, cells transfected with hairpin expression construct. The probe is complementary to the antisense. In Lanes 24, the siRNA encoding DNA constructs were co-transfected with the inducible EGFP construct. The hairpin product appears smaller than the individually expressed siRNAs, demonstrating processing of the hairpin loop. B and C. PCR amplification of transfected PCR constructs. B. PCR amplification of non-specific siRNA encoding DNA from fluorescence activated cell sorting (FACS) sorted EFGP positive and negative cells. The non-functional construct is detected in all cell fractions. Lanes 1 and 4 show the amplification results from the EGFP positive fractions. Lanes 2 and 3 show the amplification results from the EGFP negative fractions. C. PCR amplification of functional hairpin expression construct from FACS sorted, EGFP expressing and non-expressing cells. The amplification results show the presence of the functional siRNA only in the EGFP negative fractions (lanes 2-3). In lane 4, there is a small amount of amplified product, perhaps derived from some contaminating of EGFP negative cells. NC indicates negative PCR controls.

An HIV rev sequence fused to the enhanced green fluorescent protein (EGFP)-coding sequence (Lee et al., 2002) was used to test the PCR amplified siRNA encoding DNA for efficacy in cells. This construct was inserted in the Ecdysone-inducible pIND vector system (Invitrogen). The vector was then transfected into 293 cells, which stably express the trans-activator for the inducible promoter. Use of this system results in strong EGFP expression following addition of Ponasterone A (Invitrogen) to the culture media (FIG. 3A).

A stable cell line expressing both the trans-activator and target constructs may be preferable when multiple siRNA genes are being tested, but co-transfection with the target-EGFP fusion construct provides a rapid and sensitive test for siRNA efficacy. Target sequence cDNAs can be readily cloned into this inducible vector system to create the desired EGFP fusion. Utilizing this system, an effective siRNA expressed from the PCR product will inhibit EGFP expression, allowing either FACS or microscopic based analyses of siRNA function.

To test the PCR approach, U6 cassettes containing either sense or antisense siRNA genes (FIG. 1A) or a hairpin construct encoding both the sense and antisense si-RNAs (FIG. 1C) were amplified. The PCR products were column purified.

Figure 2:
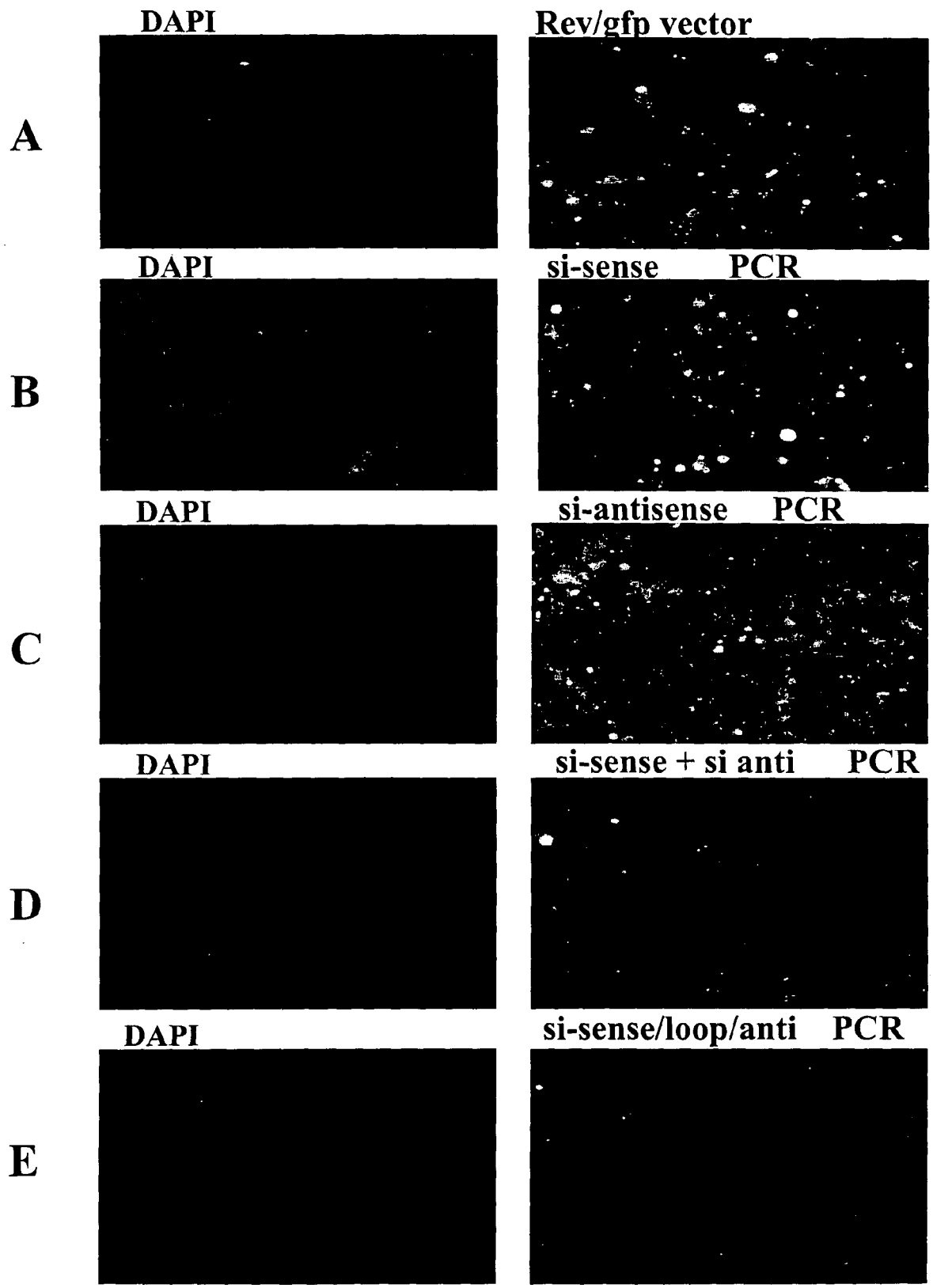
FIG. 2 shows the inhibition of enhanced green fluorescent protein (EGFP) expression using siRNA-containing PCR cassettes transfected in 293 cells. The PCR cassettes containing either the sense, antisense, or both sense and antisense siRNAs were co-transfected with the target construct into 293 cells expressing the Ecdysone trans-activator. The human immunodeficiency virus (HIV) rev target is fused to the green fluorescent protein mRNA which is expressed from an inducible promoter. After adding Ponasterone A, EGFP expression can be detected in the control cells (A), but not in cells transfected with either a mixture of sense and antisense siRNA expressing PCR products (D), or with the PCR cassette expressing the hairpin construct (E). Panels B and C depict co-transfection of cells with target and PCR cassettes expressing sense alone (B) or antisense alone (C). The Rev-EGFP protein is primarily in the cell nucleolus as a consequence of the nucleolar localizing signal in the Rev portion.

The purified PCR products were then co-transfected with the inducible rev-EGFP fusion construct into the Ecdysone trans-activator expressing cell line. 48 hours post transfection, Ponasterone A was added to the culture to induce target mRNA expression. Using this system a strong and specific down regulation of EGFP expression by the siRNAs was detectable 12 hours post induction (FIG. 2). Transfection of a control cassette, such as a U6 expression cassette expressing only the sense (FIG. 2B), the antisense (FIG. 2C) or an irrelevant siRNA (not shown), had no effect on expression of EFGP. However, when cassettes expressing the sense and antisense siRNAs were co-transfected with the target, or when a single cassette containing the hairpin siRNA gene was used, a specific and effective down regulation of the target was detected (FIGS. 2D and E). The best and most reproducible inhibition (nearly 90%) was obtained with the hairpin siRNA expressing cassette. These results were reproduced independently 5 times. The selected length and sequence of the 9 base loop (UUUGUGUAG) used for these experiments is based upon phylogenetic comparisons of loops found in several microRNA precursors. When using the above loop, the sequence of the siRNA sense strand preferably should not include a U as the 3' base since this would create a stretch of 4 Uridines, which can serve as a Pol III terminator element.

The above results indicate that the transfection-PCR methodology of the present invention can be easily used to rapidly test siRNA targeting and function in cells.

An important element in the design of effective siRNAs is the selection of siRNA/target sequence combinations that yield the best inhibitory activity. This can be accomplished using siRNAs and transfection procedures, but this can be costly and time consuming. By utilizing the PCR strategy, several siRNA genes can be simultaneously tested in a single transfection experiment.

In order to facilitate the identification of functional siRNA genes, a "stuffer" tag sequence was inserted directly after the Pol III transcription terminator (see FIG. 1). By utilizing this tag, a transfected PCR cassette can be amplified from transfected cells and the siRNA sequence subsequently identified (FIG. 1D). This can be accomplished by utilizing the 5' U6 universal primer and a primer complementary to the tag sequence (FIG. 1D). The tag sequence can start with the 6 Ts of the Ter sequence followed by a restriction site that can be used for subsequent cloning, and a "stuffer" of 6 extra nucleotides (for a total of 18 nt). A mix of several siRNAs can be simultaneously co-transfected with the inducible target-EGFP cassette into the cell line containing the trans-activator. Twelve hours after adding Ponasterone A, the EGFP negative and EGFP positive cells can be collected by FACS sorting, and the DNAs harvested from both fractions. The isolated PCR products can then be transfected for a second round of selection and amplification to select those siDNA genes that express the most potent siRNAs. The resultant PCR products can then be cloned and sequenced. The functional siRNA can be identified since it would be absent in the cells still expressing EGFP but present in the EGFP negative fraction.

Using variations of the above approach, several expression cassettes may be created and used to simultaneously screen for siRNA sensitive target sites on any given mRNA. The target sequence may be fused to EFGP or a similar reporter, and screening can be rapidly accomplished via FACS analyses and sorting. This strategy can be utilized for endogenous targets when there is a positive selection or a FACS sortable phenotype available. An amplification strategy in accordance with the present invention offers a rapid and inexpensive approach for intracellular expression of siRNAs and subsequent testing of target site sensitivity to down-regulation by siRNAs.

The present invention is further detailed in the following Examples, which are offered by way of illustration and are not intended to limit the invention in any manner.

Example 1

Target Construction and Location of the siRNA Target Site

The HIV-rev sequence followed by the EGFP gene cloned in the pIND-inducible vector (Invitrogen) as previously described (Lee et al., 2002) was selected as a target site for siRNA. The selection of the accessible target site for the siRNA was based on previous work and was shown to be an effective siRNA target using the U6 expression system (Lee et al., 2002). The sequence of the target site is: 5' GCCTGTGC-CTCTTCAGCTACC 3' [SEQ ID NO: 1], which is located 213 nucleotides downstream of the rev-AUG start codon.

Example 2

Polymerase Chain Reaction

PCR reactions were performed using a plasmid containing the human U6 promoter as template. The 5' oligonucleotide (5'U6 universal primer) is complementary to 29 nucleotides at the 5' end of the U6 promoter (bold italics) 5'ATCGCA-GATCTGGATCCAAGGTCGGGCAGGAAGAGGGCCT3' [SEQ ID NO: 2] and was used for all PCR steps. The 3' oligonucleotides, which contain either the sense, antisense, or both sense and antisense, are depicted in FIG. 1 and described herein. The last 20 nucleotides at the 3' end of all 3' PCR primers are complementary to the last 20 nucleotides of the U6 promoter which is: 5'GTGGAAAGGACGAAA-CACCG3' [SEQ ID NO: 3]. All PCR reactions were carried out as follows: 1 min. at 94° C., 1 min at 55° C. and 1 min at 72° C. for 30 cycles. The PCR primers were kinased with non-radioactive ATP prior to amplification and purified on Qiagen columns prior to using them in the PCR reactions. The PCR products were also purified on Quiagen columns.

The sequences of the siDNA encoding oligos are:

```
1. Sense for siRNA rev-
5'CGAAAAGGCCTAAAAAAGGTAGCTGAAGAGGCACAGGCGGTGTTTCGTCCTTTCCACAAGATATATAA 3' [SEQ ID NO: 4]

2. Antisense for siRNA rev-
5'CGAAAAGGCCTAAAAAAGCCTGTGCCTCTTCAGCTACCGGTGTTTCGTCCTTTCCACAAGATATATAA 3' [SEQ ID NO: 5]
```

-continued

3. Hairpin siRNA oligo 1- sense
5'TACACAAA*GGTAGCTGAAGAGGCACAGGC*GGTGTTTCGTCCTTTCCACAAGATATATAA 3'  [SEQ ID NO: 6]

4. Hairpin siRNA oligo 2-antisense
5'CGAAAAGGCCTAAAAAA*GCCTGTGCCTCTTCAGCTACCC*TACACAAAGG 3'  [SEQ ID NO: 7]

The italicized sequences are the siRNA encoding sequences.

Example 3

Cell Lines and Culture Conditions 293 cells were grown DMEM (Irvine Scientific, Santa Ana, Calif.) supplemented with 10% fetal calf serum (Irvine Scientific), 1 mM L-glutamine, and 100 units/ml of penicillin/streptomycin. The Ecdysone-inducible stable A293 clone has been previously described (Lee et al., 2002) and it was maintained in DMEM containing 100 µg/ml of Zeocin (Invitrogen).

Example 4

Transfection Conditions for siRNA-PCR Products 250 ng of the target plasmid were co-transfected with either: 1) 50 ng of the PCR cassette expressing the sense, and/or 50 ng of the cassette expressing the antisense siRNA; or 2) 100 ng of the single cassette expressing both the sense and antisense linked by a 9 nt. loop. As few as 25 ng of the stem loop siRNA was effective in blocking target expression. An irrelevant stem-loop siRNA was used as an additional control and did not result in any effect on target expression (not shown).

To facilitate the transfection of the small amounts of PCR amplified DNA, 400 ng of Bluescript plasmid were added to each reaction to serve as carrier. 5 µM Ponasterone A was added to the culture media 48 hours after transfection, and the cells were analyzed for EGFP expression 12 hours following induction. Transfections were performed in 6 well plates using Lipofectamine Plus™ reagent (Life Technologies, GibcoBRL) as described by the manufacturer. For microscope imaging, cells were grown and transfected on glass coverslips treated with 0.5% gelatin (Sigma). 12 hours post-induction the coverslips were lifted from the 6 well plate and treated for 10 min. at room temperature with 4% PFA for cell fixation. Cell nuclei were visualized adding DAPI to the mounting solution. Down regulation of the rev-EGFP mRNA was quantitated by FACS analyses.

Example 5

Northern Analyses

Total RNA was isolated using RNA STAT-60 (TEL-TEST B Inc., Friendswood, Tex.) according to the manufacturer's instructions. 5 µg of total RNA was fractionated by 8M-6% PAGE, and transferred onto Hybond-N+ membrane (Amersham Pharmacia Biotech). A $^{32}$P-radiolabeled 21-mer probe complementary to the si-antisense RNA was used for the hybridization reactions, which were performed for 16 hours at 37° C. A 21-mer DNA oligonucleotide was electrophoresed alongside the RNA samples and used as size and hybridization control (not shown).

Example 6

Direct Amplification of siRNAs from Cell Lysates

EGFP-negative and -positive cell fractions were collected by FACS sorting. The cell pellets were recovered immediately by centrifugation of the sorted fractions. The pellets were lysed in 50 mM KCl, 10 mMTris-HCl (pH 8.0), 1.25 mM MgCl$_2$, 0.45% NP40, 0.45% Tween, and 0.75 µg/µl Proteinase K at 37° C. overnight. After 10 minutes heat inactivation at 95° C., 3 µl of the cell lysates were used directly in PCR reactions.

Example 7

15 ng of the PCR amplified gene encoding the siRNA hairpin targeting the HIV-rev site, along with 15 ng of an irrelevant siRNA PCR product were co-transfected with the inducible target-EGFP cassette into the 293 cell line expressing the trans-activator. Twelve hours post transfection, Ponasterone A was added to induce EGFP expression and the EGFP negative and positive cells were FACS sorted. The cell pellets from both the EGFP negative and positive cells were collected by centrifugation, lysed overnight in lysis buffer and the DNAs amplified directly by PCR utilizing the appropriate primer sets. Two different 3' primers that discriminate between the two different siRNA encoding DNA cassettes were used. It was expected that the non-functional siRNA expression cassette should be detectable by PCR amplification in both cell fractions, whereas the functional siRNA expression cassette would only be detectable in the EFGP negative fraction since its products would have functionally downregulated EGFP expression. The results of two independent experiments are shown in FIGS. 3B and C. In both cases, the non-functional siRNA encoding gene was PCR amplified from all fractions (FIG. 3B), whereas the functional siRNA encoding expression construct was primarily detected in the EGFP negative cell fractions (FIG. 3B).

Example 8

Anti-HIV U6+1 short hairpin siRNA (shRNA) PCR products were produced by PCR using a U6+1 promoter construct as template (pTZU6+1), a universal 5' primer, and a specific 3' primer. The primers are shown in Table 1 in the standard 5' to 3' orientation. The shRNAs were designed to be transcribed in the sense target sequence-loop-antisense target sequence-UUUUU (pol3 terminator) format. The sequence of the universal 5' primer, which anneals to the 5' end of the U6+1 promoter, also is shown in Table 1. Table 1 further shows the corresponding sequence of the 3' end of expected PCR product (the upper, coding strand is shown in the standard 5' to 3' orientation), beginning with the 3' end of the U6+1 promoter, ending with the +1 start site of transcription, followed by the sequences coding for the hairpin RNA (sense target/loop/anti-sense), the Pol III terminator, Bgl2 site and extra nucleotides. The sequences of the 3' primers also are shown in Table 1 following the sequence of each PCR product.

Table 1 also shows a SELEX 2144 tRNA$^{Lys3}$-tat/rev target 21-stem shRNA.

Example 9

PCR-amplified expression cassettes expressing anti-tat siRNA were found to potently inhibit HIV infection. PCR amplified short hairpin RNA encoding genes U6+1NLS1(tat/rev)shRNA, versus the same gene in a plasmid vector (pBS U6+1 NLS1 (tat/rev)shRNA), in the amounts indicated in FIG. 4, were co-transfected with 0.5 micrograms of HIV pNL4-3 into 293 cells and the viral encoded p24 antigen output was measured over three days. As controls, empty vector backbones (pBS or pTZU6+1) or a triple mutation at sites 9, 10 and 11 of the anti-tat shRNA (U6+1mNLS1shRNA (PCR product) or pBSU6+1mNLS1shRNA (plasmid based system)) were transfected as a PCR amplified gene with HIV-1. The results in FIG. 4 show the several logs worth of inhibition obtained using cassettes produced according to the present invention as compared to the same gene in a plasmid vector.

Figure 4:
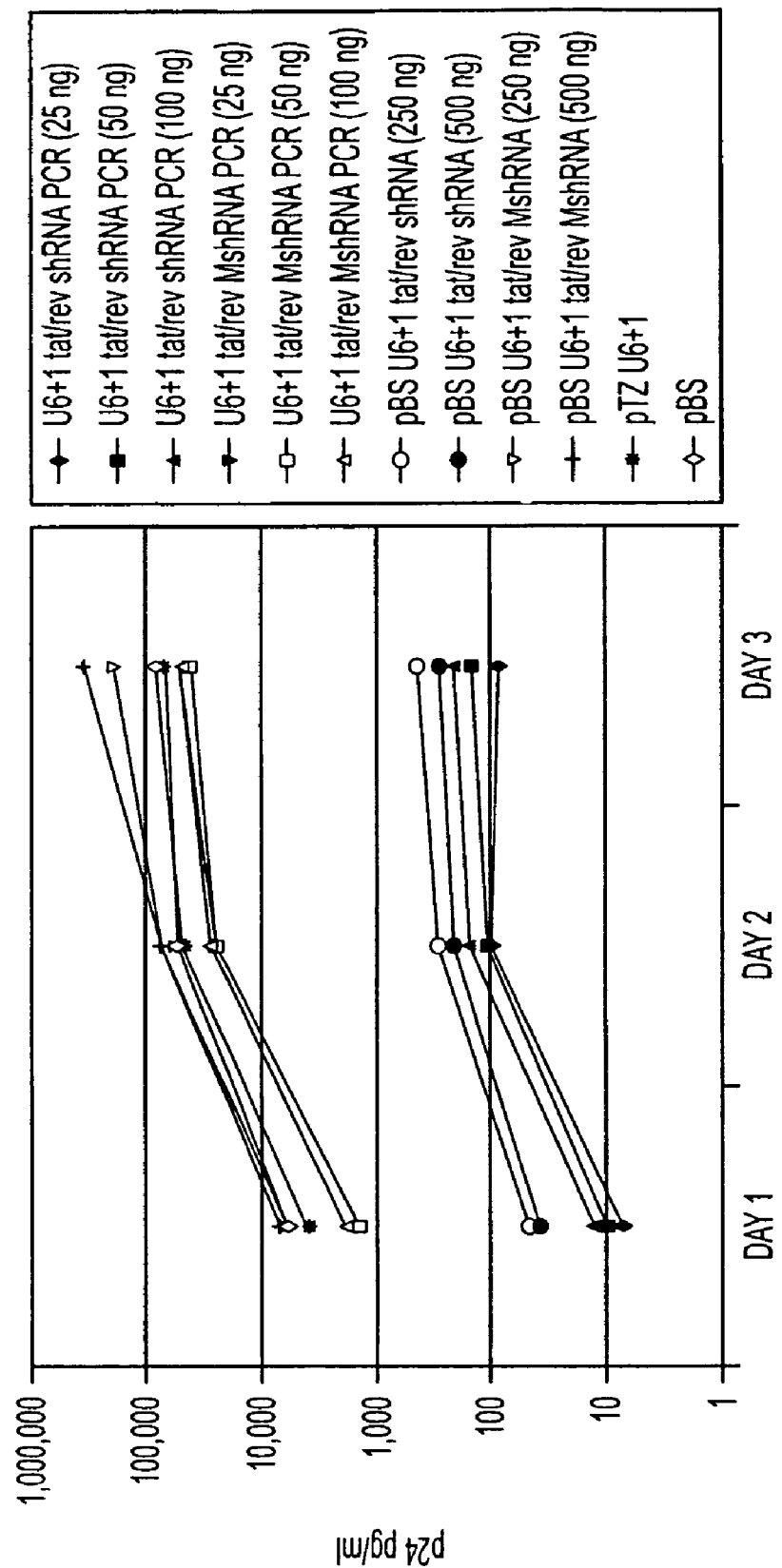
FIG. 4 is a graph showing a comparison of HIV inhibition by shRNAs expressed from a PCR product and plasmids.

FIG. 4 shows that the U6+1 tat/rev shRNA specifically mediates comparable HIV inhibition at equivalent molar ratios, regardless of whether the cassette is transfected as a PCR product directly or is part of a plasmid backbone. This panel also illustrates that small amounts of an shRNA construct can mediate substantial HIV inhibition with susceptible target sites.

Example 10

Figure 5:
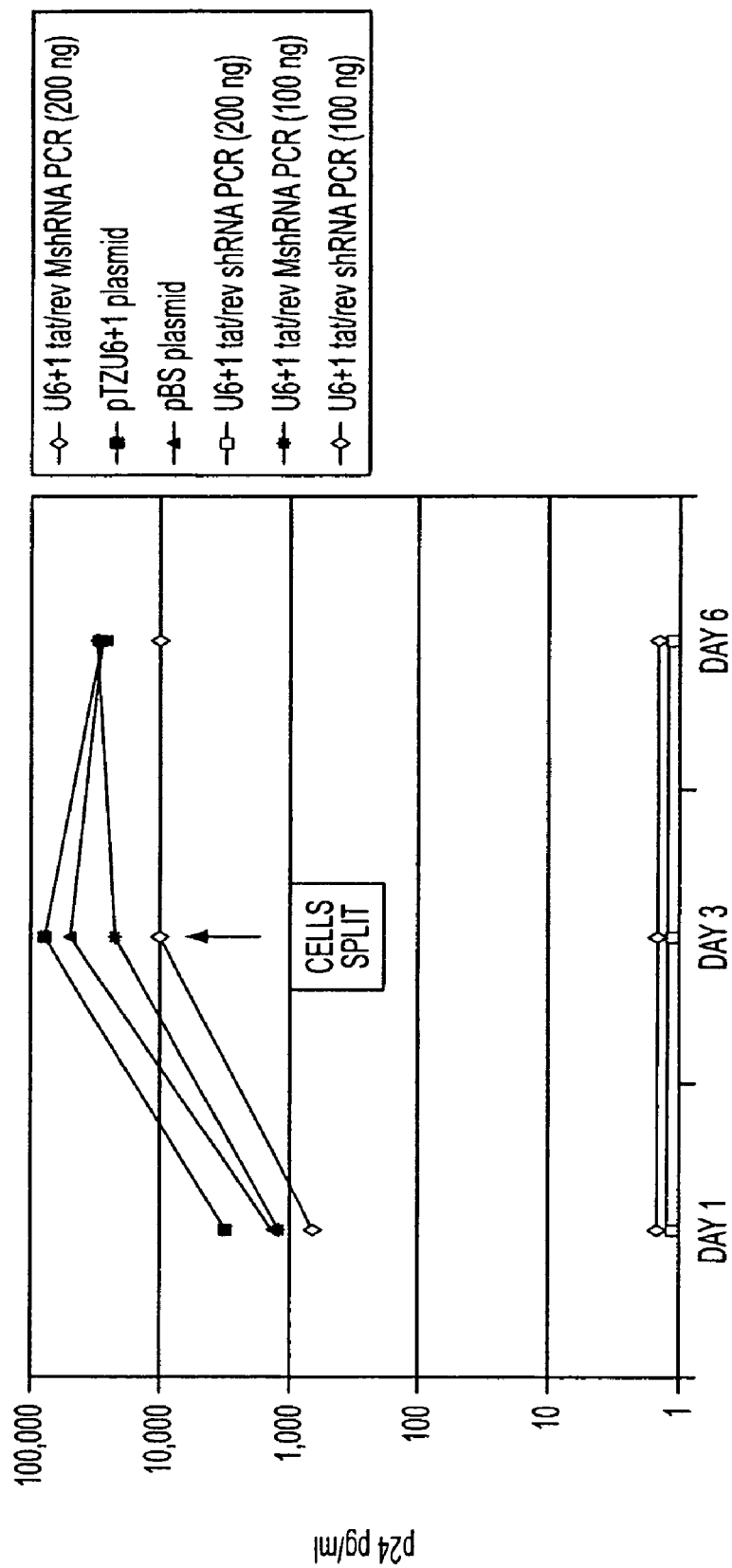
FIG. 5 is a graph showing the persistence of HIV inhibition by shRNAs expressed from PCR products in accordance with the present invention.

FIG. 5 shows the persistence of HIV inhibition by shRNAs expressed from PCR products. HIV co-transfection inhibition assays were performed as described in Example 9, using the U6+1 tat/rev shoRNA U6+1 tat/rev mutant shRNA constructs as positive and negative controls. After collecting viral supernatant on day 3, the confluent 293 cells were reseeded in fresh medium at 10% confluency and allowed to expand for another 3 days before collecting viral supernatants for assay. FIG. 5 shows that PCR product-mediated HIV inhibition persists for at least six days under these experimental conditions.

Example 11

Figure 6:
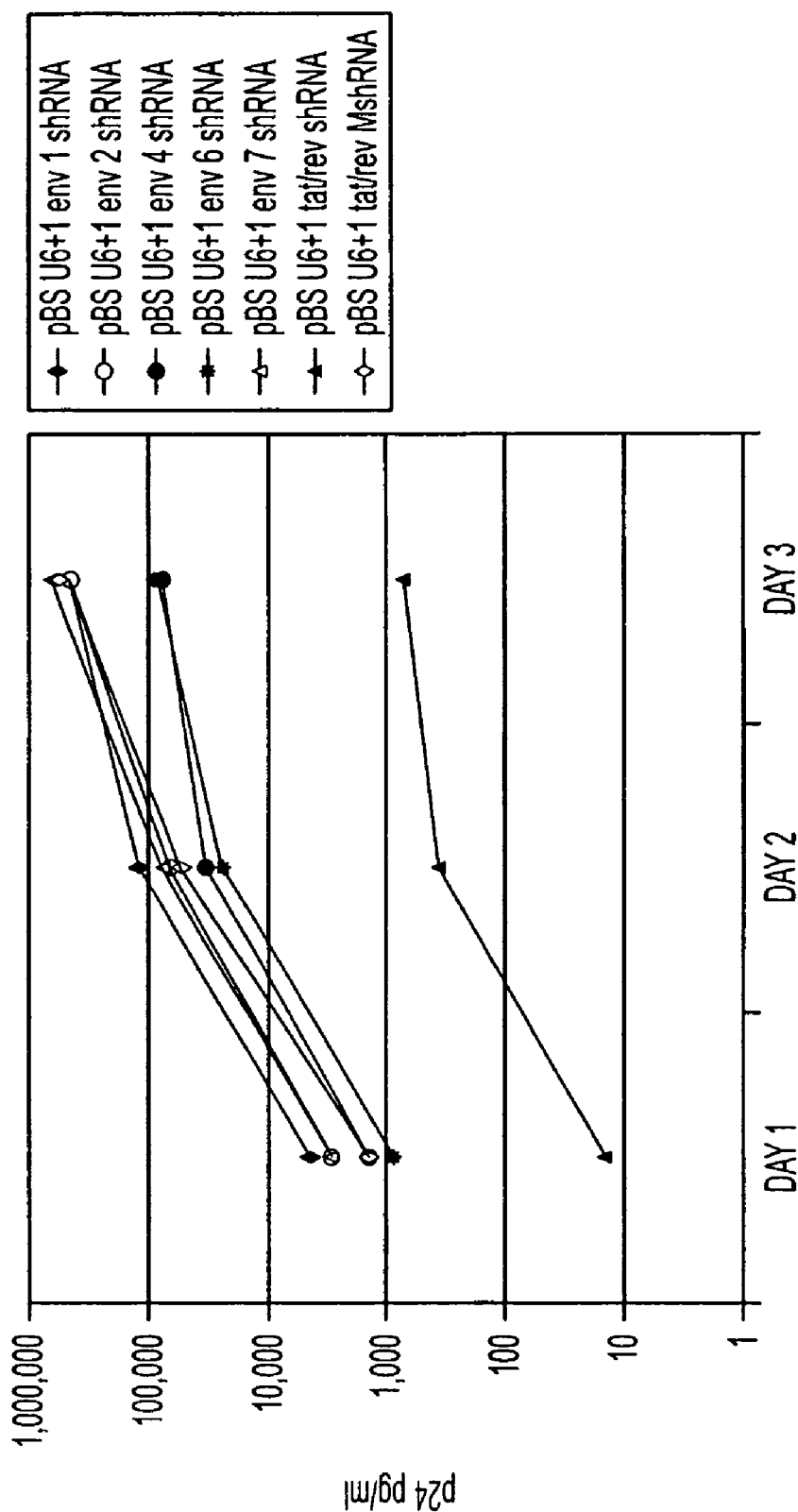
FIG. 6 is a graph showing the results of an HIV inhibition test using cloned U6+1 shRNA constructs.

FIG. 6 shows the results of an HIV inhibition test using cloned U6+1 env shRNA constructs (Table 1). Each well of a 6-cluster plate containing 293 cells at ~50% confluency was co-transfected with 0.5 μg of cloned plasmid shRNA and 0.5 μg pNL4-3 proviral DNA per well of a 6-cluster plate using Lipfectamine Plus according to the manufacturer's instructions. Aliquots of viral supernatants were taken at the indicated times and assayed for p24 antigen. Tat/rev, positive control for inhibition; Mtat/rev, negative control for inhibition mismatched with target site at positions 10, 11, and 12 relative to 5' end of processed antisense strand.

Example 12

Figure 7:
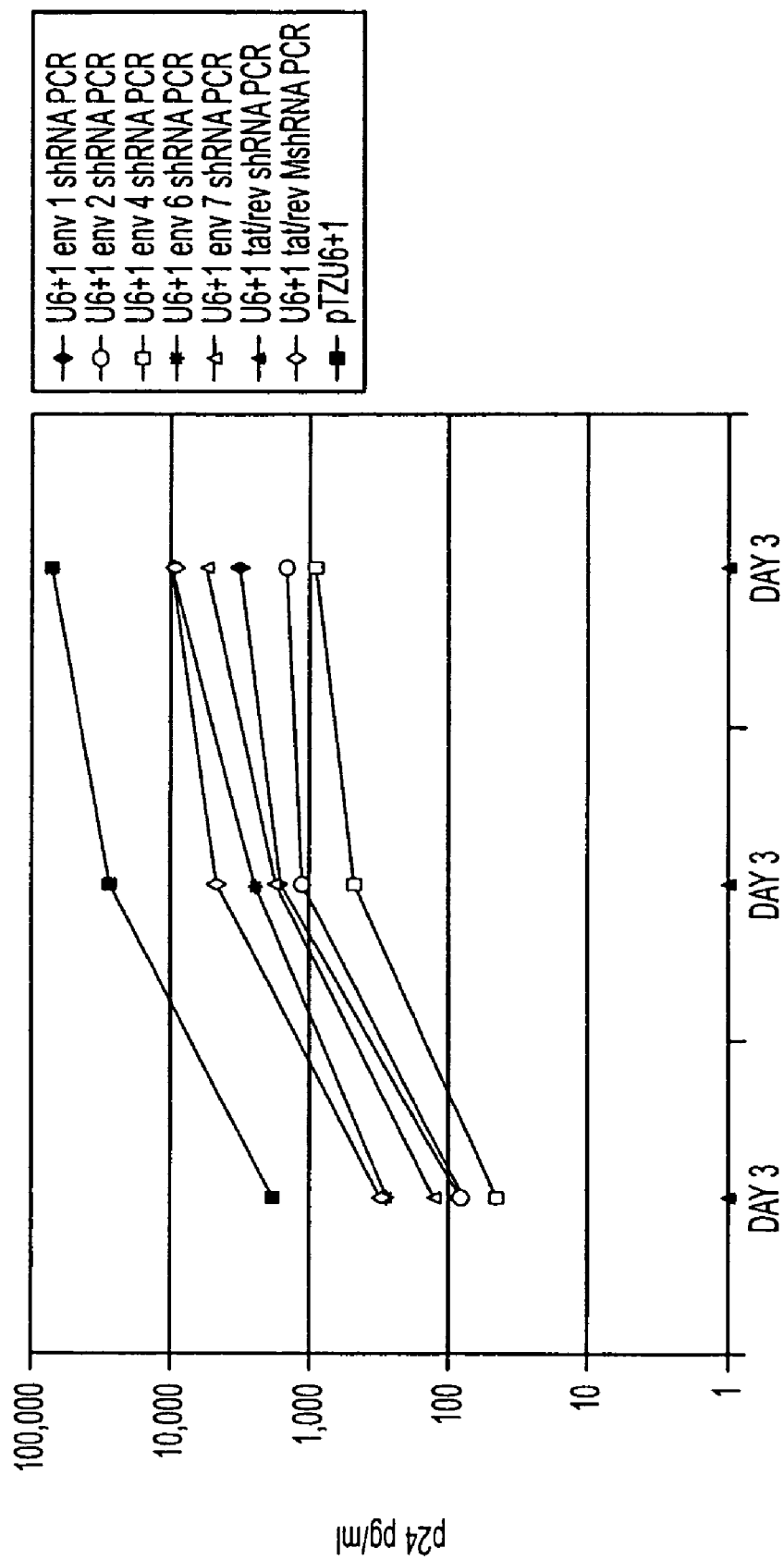
FIG. 7 is a graph showing the results of HIV inhibition assays using a purified U6+1 shRNA PCR product in accordance with the present invention.

FIG. 7 shows the results of HIV inhibition assays, using 200 ng of each U6+1 env shRNA PCR product purified from a set of PCR reactions. pTZU6+1 is a negative control plasmid containing the U6+1 promoter.

Example 13

Figure 8:
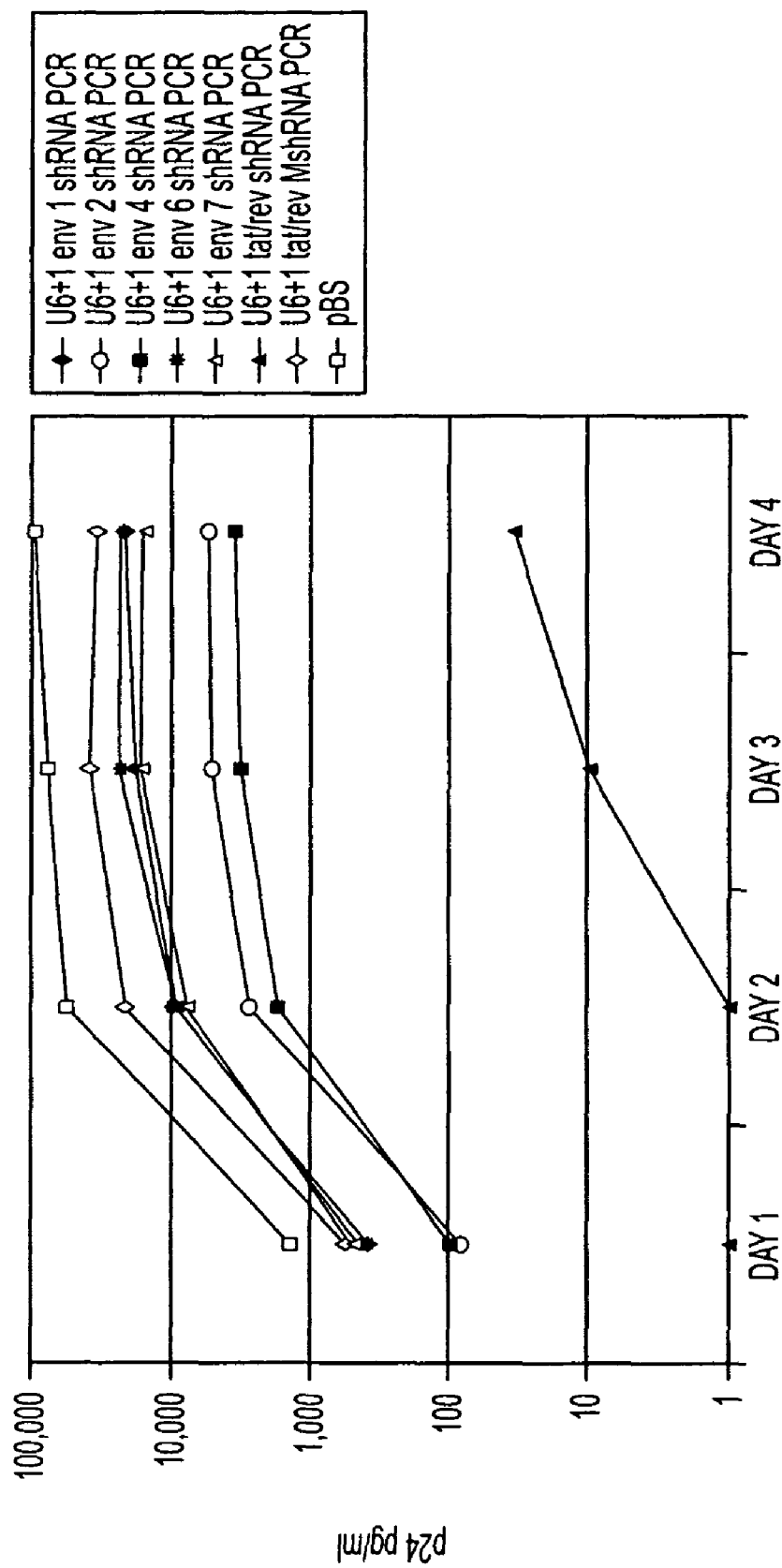
FIG. 8 is a graph showing the results of HIV inhibition assays using a purified U6+1 shRNA product in accordance with the present invention.

FIG. 8 shows HIV inhibition by U6+1 env shRNAs, using 100 ng each U6+1 env shRNA PCR product purified from another set of PCR reactions. U6+1 tat/rev shRNA and U6+1 tat/rev Mutant shRNA PCR products were included as controls.

The publications and other materials used herein to illuminate the background of the invention, and provide additional details respecting the practice of the invention, are incorporated herein by reference as if each was individually incorporated herein by reference.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

TABLE 1

Universal 5' primer

ATAAGAATGCGGCCGCCCCCGGGATCCAAGGTCGGG (SEQ ID NO: 8)  Underlining indicates sequence homologous to 5' end of U6+ promoter HIV-1 env 1 Construct CTTGTGGAAAGGACGAAACACCG CAACACAACTGTTTAATAGTA TTTGTGTAG TACTATTAAACAGTTGTGTTG TTTTTT AGATCT TCC [SEQ ID NO: 9]
GAACACCTTTCCTGCTTTGTGGC GTTGTTGTTGACAAATTATCAT AAACACATC ATGATAATTTGTCAACACAAC AAAAAA TCTAGA AGG [SEQ ID NO: 10]

GGAAGATCTAAAAAACAACACAACTGTTTAATAGTACTACACAAATACTATTAAACAGTTGTGTTGCGGTGTTTCGTCCTTTCCACAAG [SEQ ID NO: 10]

HIV-1 env 2 Construct

CTTGTGGAAAGGACGAAACACCG CACAATCACACTCCCATGCAG TTTGTGTAG CTGCATGGGAGTGTGATTGTG TTTTTT AGATCT TCC [SEQ ID NO: 11]
GAACACCTTTCCTGCTTTGTGGC GTGTTAGTGTGAGGGTACGTC AAACACATC GACGTACCCTCACACTAACAC AAAAAA TCTAGA AGG [SEQ ID NO: 12]

GGAAGATCTAAAAAACACAATCACACTCCCATGCAGCTACACAAACTGCATGGGAGTGTGATTGTGCGGTGTTTCGTCCTTTCCACAAG [SEQ ID NO: 12]

HIV-1 env 4 Construct

CTTGTGGAAAGGACGAAACACCG GAGGAGGCGATATGAGGGAC TTTGTGTAG GTCCCTCATATCGCCTCCTCC TTTTTT AGATCT TCC [SEQ ID NO: 13]
GAACACCTTTCCTGCTTTGTGGC CTCCTCCGCTATACTCCCTG AAACACATC CAGGGAGTATAGCGGAGGAGG AAAAAA TCTAGA AGG [SEQ ID NO: 14]

GGAAGATCTAAAAAAGGAGGAGGCGATATGAGGGACCTACACAAAGTCCCTCATATCGCCTCCTCCGGTGTTTCGTCCTTTCCACAAG [SEQ ID NO: 14]

HIV-1 env 6 Construct

CTTGTGGAAAGGACGAAACACCG TGTCTGATATAGTGCAGCAGC TTTGTGTAG GCTGCTGCACTATATCAGACA TTTTTT AGATCT TCC [SEQ ID NO: 15]
GAACACCTTTCCTGCTTTGTGGC ACAGACTATATCACGTCGTCG AAACACATC CGACGACGTGATATAGTCTGT AAAAAA TCTAGA AGG [SEQ ID NO: 16]

GGAAGATCTAAAAAATGTCTGATATAGTGCAGCAGCCTACACAAAGCTGCTGCACTATATCAGACACGTGTTTCGTCCTTTCCACAAG [SEQ ID NO: 16]

HIV-1 env 7 Construct

CTTGTGGAAAGGACGAAACACCG TCTGTTGCAACTCACAGTCTG TTTGTGTAG CAGACTGTGAGTTGCAACAGA TTTTTT AGATCT TCC [SEQ ID NO: 17]
GAACACCTTTCCTGCTTTGTGGC AGACAACGTTGAGTGTCAGAC AAACACATC GTCTGACACTCAACGTTGTCT AAAAAA TCTAGA AGG [SEQ ID NO: 18]

GGAAGATCTAAAAAATCTGTTGCAACTCACAGTCTGCTACACAAACAGACTGTGAGTTGCAACAGACGTGTTTCGTCCTTTCCACAAG [SEQ ID NO: 18]

TABLE 1-continued

HIV-1 tat/rev: positive control
CTTGTGGAAGGACGAAACACCG CGGAGACAGCGACGAAGAGC TTTGTGTAG GCTCTTCGTCGTCTCCGC TTTTTT AGATCT TCC [SEQ ID NO: 19]
GAACACCTTCCTGCTTTGTGGC GCCTCTGTCGCTGCTTCTCG AAACACATC CGAGAAGCAGCGACAGAGGCG AAAAAA TCTAGA AGG [SEQ ID NO: 20]

GGAAGATCTAAAAAAGCGGAGACAGCGACGAAGAGCCTCTTCGTCGCTGTCTCCGCGGTGTTTCGTCCTTTCCACAAG [SEQ ID NO: 20]

HIV-1 tat/rev: negative control (nucleotides in red are mismatched to pNL4-3 sequence)
CTTGTGGAAGGACGAAACACCG CGGAGACATATACGAAGAGAC TTTGTGTAG GCTCTTCGTATATGTCTCCG TTTTTT AGATCT TCC [SEQ ID NO: 21]
GAACACCTTCCTGCTTTGTGGC GCCTCTGTATATGCTTCTCG AAACACATC CGAGAAGCATATACAGAGGCG AAAAAA TCTAGA AGG [SEQ ID NO: 22]

GGAAGATCTAAAAAAGCGGAGACATATACGAAGAGCCTACACAAAGCTCTTCGTATATGTCTCCGCGGTGTTTCGTCCTTTCCACAAG [SEQ ID NO: 22]

HIV-1 tat/rev: positive control with BstG1 loop
changed loop nucleotides

CTTGTGGAAGGACGAAACACCG CGGAGACAGCGACGAAGAGC TTTGTGTAG GCTCTTCGTCGCTGTCTCCGC TTTTTT AGATCT TCC [SEQ ID NO: 23]
GAACACCTTCCTGCTTTGTGGC GCCTCTGTCGCTGCTTCTCG AAACACATC CGAGAAGCAGCGACAGAGGCG AAAAAA TCTAGA AGG [SEQ ID NO: 24]

GGAAGATCTAAAAAACCGGAGACAGCGACGAAGAGCCTGTACAAAGCTCTTCGTCGCTGTCTCCGGTGTTTCGTCCTTTCCACAAG [SEQ ID NO: 24]

HIV-1 nef target shRNA
 TTCCAGTCAGACCT [SEQ ID NO: 25]        (9016-9029) Larrson, SF2 (B-type) consensus target
TTTTTCCAGTCACACCTCAGTACCTTT [SEQ ID NO: 26]     (8987-9013) pNL4-3 underlined area, 21-mer shRNA target CTTGTGGAAGGACGAAACACCG TTCCAGTCACACCTCAGTAC TTCCAGTGAGTGTGACTGAA TTTTTT AGATCT TAACC [SEQ ID NO: 27]
GAACACCTTCCTGCTTTGTGGC AAGGTCAGTGTGGAGTCCATG AAACACATC CATGGACTCCACACTGACCTT AAAAAA TCTAGA ATTGG [SEQ ID NO: 28]

GGTTAAGATCTAAAAAATTCAGTCACACTCACTCCAGGTACCTACACAAAGTACCTGAGGTGTGACTGGAACGGTGTTTCGTCCTTTCCACAAG [SEQ ID NO: 28]

HIV-1 pol target shRNA
  GCTCTATTAGATACAGGAG [SEQ ID NO: 29]      pNL4-3 2315 (start)
GAAGCTCTATTAGATACAGGAGCAGAT SEQ ID NO: 30]   pNL4-3 context shRNA 21-mer CTTGTGGAAGGACGAAACACCG CTCTATTAGATACAGGAGCA TTTGTGTAG TGCTCCTGTATCTAATAGAGC TTTTTT AGATCT TAACC [SEQ ID NO: 31]
GAACACCTTCCTGCTTTGTGGC GAGATAATCTATGTCCTCGT AAACACATC ACGAGGACATAGATTATCTCG AAAAAA TCTAGA ATTGG [SEQ ID NO: 32]

GGTTAAGATCTAAAAAAGCTCTATTAGATACAGGAGCACTACACAAATGCTCCTGTATCTAATAGAGCGGTGTTTCGTCCTTTCCACAAG [SEQ ID NO: 32]

TABLE 1-continued

HIV-1 rev target shRNA (site II)
CTTGTGGAAAGGACGAAACACCG CCTGTGCCTCTTCAGCTACC GAAGCTTG GGTAGCTGAAGAGGCACAGGC TTTTTTCATGCATCATGTCCCGGGGGA [SEQ ID NO: 33]

ACACCTTTCCTGCTTTGTGGC GGACACGGAGAAGTCGATGG CTTCGAAC CCATCGACTTCTCCGTCCG AAAAAAGTACGTACGTACAGGGCCCCCT [SEQ ID NO: 34]

TCCCCCGGGACATGCATGCATGAAAAAAAGCCTGTGCCTCTTCCAGCTACCCAAGCTTC GGTAGCTGAAGAGGCACAGGCGGGTGTTTCGTCCTTTCCACA [SEQ ID NO: 34]

SELEX 2144 tRNA^Lys3^-tat/rev target 21-stem shRNA)
5' primer ACGCGTCGACGCCCGGATAGCTCGGTCGG [SEQ ID NO: 35]

SELEX 2144 sequence changes
                G          G                        G          G A
wild-type tRNA^Lys3^ GTCGACGCC CGGATAGCTC AGTCGGTAGA GCATCAGACT TTTCAATCTGA GGGTCCAGGG TTCAAGTCC TGTTCGGGCGCCA [SEQ ID NO: 36]

3' end of SELEX 2144 tRNA^Lys3^ sequence/ siRNA sense/loop/siRNA anti-sense/ pol3 term/ Bgl2
GTTCGAGTCCTGTTCGTGCACCA GCGGAGACAGGCGACGAAGAGC TTTGTGTAG GCTCTTCGTCGCTGTCTCGC TTTTTT AGATCT TCC [SEQ ID NO: 37]
CAAGCTCAGGACAAGCACGTGGT CGCCTCTGTCCGCTGCTTCTCG AAACACATC CGAGAAGCAGCGACAGAGGCG AAAAAA TCTAGA AGG [SEQ ID NO: 38]

GGAAGATCTAAAAAAGCGGAGACAGCGACGAAGAGCCTACACAAAGCTCTTCGTCGCTGTCTCCCGCTGGCTGAGGGCAGGCACGTGCTTAA 3' primer [SEQ ID NO: 38]

REFERENCES

1. Moss, E. G., *RNA interference: it's a small RNA world.* Curr Biol, 2001. 11(19): p. R772-5.
2. Bernstein, E., A. M. Denli, and G. J. Hannon, *The rest is silence.* Rna, 2001. 7(11): p. 1509-21.
3. Elbashir, S. M., W. Lendeckel, and T. Tuschl, *RNA interference is mediated by 21- and 22-nucleotide RNAs.* Genes Dev, 2001. 15(2): p. 188-200.
4. Elbashir, S. M., et al., *Duplexes of 21-nucleotide RNAs mediate RNA interference in cultured mammalian cells.* Nature, 2001. 411(6836): p. 494-8.
5. Bernstein, E., et al., *Role for a bidentate ribonuclease in the initiation step of RNA interference.* Nature, 2001. 409(6818): p. 363-6.
6. Hammond, S. M., et al., *Argonaute2, a link between genetic and biochemical analyses of RNAi.* Science, 2001. 293 (5532): p. 1146-50.
7. Lee, N. S., et al., *Expression of small interfering RNAs targeted against HIV-1 rev transcripts in human cells.* Nat Biotechnol, 2002. 20(5): p. 500-5.
8. Miyagishi, M. and K. Taira, *U6 promoter driven siRNAs with four uridine 3' overhangs efficiently suppress targeted gene expression in mammalian cells.* Nat Biotechnol, 2002. 20(5): p. 497-500.
9. Paul, C. P., et al., *Effective expression of small interfering RNA in human cells.* Nat Biotechnol, 2002. 20(5): p. 505-8.
10. Brummelkamp, T. R., R. Bernards, and R. Agami, *A system for stable expression of short interfering RNAs in mammalian cells.* Science, 2002. 296(5567): p. 550-3.
11. Ketting, R. F., et al., *Dicer functions of RNA interference and in synthesis of small RNA involved in developmental timing in C. elegans.* Genes Dev, 2001. 15(20): p. 2654-9.
12. Yu, J. Y., S. L. DeRuiter, and D. L. Turner, *RNA interference by expression of short-interfering RNAs and hairpin RNAs in mammalian cells.* Proc Natl Acad Sci USA, 2002. 99(9): p. 6047-52.
13. Holen, T., et al., *Positional effects of short interfering RNAs targeting the human coagulation trigger Tissue Factor.* Nucleic Acids Res, 2002. 30(8): p. 1757-66.
14. Hamilton, A., et al., *Two classes of short interfering RNA in RNA silencing.* EMBO Journal, 2002. 21: p. 4671-4679.
15. Herman, J. G., et al., *Methylation-Specific PCR: A Novel PCR Assay for Methylation Status of CpG Islands.* PNAS USA, 1996. 93: p. 9821-9826.

---

What is claimed is:

1. An amplification-based method for producing at least one mammalian promoter-containing expression cassette, comprising:

(i) adding a double stranded nucleic acid comprising a mammalian promoter to an amplification reaction mixture, wherein the double stranded nucleic acid has a sense strand and an antisense strand and wherein each of the sense strand and antisense strand has a 5' end and a 3' end, wherein the mammalian promoter is capable of transcribing an RNA molecule in mammalian cells;

(ii) adding a first oligonucleotide primer to the reaction mixture, wherein the first oligonucleotide primer is complementary to the 3' end of the antisense strand of the double stranded nucleic acid;

(iii) adding a second oligonucleotide primer to the reaction mixture, wherein the second oligonucleotide primer is complementary to the 3' end of the sense strand of the double stranded nucleic acid and wherein the second oligonucleotide primer comprises a nucleotide sequence that is complementary to a nucleotide sequence that encodes (1) a sense sequence of a double stranded siRNA molecule and (2) a terminator sequence; and (iv) amplifying the double stranded nucleic acid in a polymerase chain reaction amplification comprising (a) annealing the primers to the complementary strands of the double stranded nucleic acid, (b) extending the annealed primers to produce extension products, (c) denaturing the extension products and (d) repeating the polymerase chain reaction amplification steps a sufficient number of times to produce a first amplified product comprising a first mammalian promoter-containing expression cassette, wherein the first mammalian promoter-containing expression cassette comprises (1) the mammalian promoter, (2) the sense strand of the double stranded siRNA molecule and (3) the terminator sequence.

2. The method of claim 1, wherein the amplification product is purified.

3. The method of claim 1, further comprising cloning the amplified product comprising the mammalian promoter-containing siRNA expression cassette into a cloning vector.

4. The method of claim 1, further comprising a second polymerase chain reaction amplification comprising:
(a) adding a double stranded nucleic acid comprising a mammalian promoter to an amplification reaction mixture, wherein the double stranded nucleic acid has a sense strand and an antisense strand and wherein each of the sense strand and antisense strand has a 5' end and a 3' end, wherein the mammalian promoter is capable of transcribing an RNA molecule in mammalian cells;
(b) adding a first oligonucleotide primer to the reaction mixture, wherein the first oligonucleotide primer is complementary to the 3' end of the antisense strand of the double stranded nucleic acid;
(c) adding a second oligonucleotide primer to the reaction mixture, wherein the second oligonucleotide primer is complementary to the 3' end of the sense strand of the double stranded nucleic acid and wherein the second oligonucleotide primer comprises a nucleotide sequence that is complementary to a nucleotide sequence that encodes (1) an antisense sequence of the double stranded siRNA molecule and (2) a terminator sequence; and
(d) amplifying the double stranded nucleic acid in a polymerase chain reaction amplification comprising (i) annealing the primers to the complementary strands of the double stranded nucleic acid, (ii) extending the annealed primers to produce extension products, (iii) denaturing the extension products and (iv) repeating the polymerase chain reaction amplification steps a sufficient number of times to produce a second amplified product comprising a second mammalian promoter-containing expression cassette, wherein the second mammalian promoter-containing expression cassette comprises (1) the mammalian promoter, (2) the antisense strand of the double stranded siRNA molecule and (3) the terminator sequence.

5. The method of claim 4, wherein the first and second amplification products are purified.

6. The method of claim 4, further comprising cloning the first amplified product comprising the first mammalian promoter-containing expression cassette into a cloning vector and cloning the second amplified product comprising the second mammalian promoter-containing expression cassette into a cloning vector.

7. The method of claim 1, wherein the mammalian promoter is a Pol III promoter.

8. The method of claim 7, wherein the Pol III promoter is a mammalian U6 promoter.

9. The method of claim 8, wherein the U6 promoter is a human U6 promoter.

10. The method of claim 1, wherein the sequence encoding the terminator sequence comprises a sequence of about 4-6 deoxyadenosines.

11. The method of claim 10, wherein the sequence encoding the terminator sequence comprises a sequence of 6 deoxyadenosines.

12. The method of claim 1, wherein the second oligonucleotide primer further comprises a tag sequence to identify functional siRNA encoding sequences.

13. The method of claim 12, wherein the tag sequence further comprises a restriction site useful for cloning.

14. The method of claim 4, further comprising the step of transfecting a mammalian cell in vitro with the first amplified mammalian promoter-containing expression cassette and with the second amplified mammalian promoter-containing expression cassette, wherein the sense strand of the double stranded siRNA molecule and the antisense strand of the double stranded siRNA molecule are expressed in the transfected cell, whereby a double stranded siRNA molecule is produced in the transfected cell.

15. The method of claim 14, wherein one or more of the oligonucleotide primers are modified.

16. The method of claim 15, wherein one or more of the oligonucleotide primers are modified by phosphorylation.

17. The method of claim 14, further comprising the step of screening for a target site on mRNA sensitive to the double stranded siRNA molecule produced.

18. An amplification-based method for producing a mammalian promoter-containing expression cassette, comprising:
(i) adding a double stranded nucleic acid comprising a mammalian promoter to an amplification reaction mixture, wherein the double stranded nucleic acid has a sense strand and an antisense strand and wherein each of the sense strand and antisense strand has a 5' end and a 3' end, wherein the mammalian promoter is capable of transcribing an RNA molecule in mammalian cells;
(ii) adding a first oligonucleotide primer to the reaction mixture, wherein the first oligonucleotide primer is complementary to the 3' end of the antisense strand of the double stranded nucleic acid;
(iii) adding a second oligonucleotide primer to the reaction mixture, wherein the second oligonucleotide primer is complementary to the 3' end of the sense strand of the double stranded nucleic acid and wherein the second oligonucleotide primer comprises a nucleotide sequence that is complementary to a nucleotide sequence that encodes (1) an antisense sequence of a double stranded siRNA molecule and (2) a terminator sequence; and
(iv) amplifying the double stranded nucleic acid in a polymerase chain reaction amplification comprising (a) annealing the primers to the complementary strands of the double stranded nucleic acid, (b) extending the annealed primers to produce extension products, (c) denaturing the extension products and (d) repeating the polymerase chain reaction amplification steps a sufficient number of times to produce an amplified product comprising a first mammalian promoter-containing expression cassette, wherein the first mammalian promoter-containing expression cassette comprises (1) the mammalian promoter, (2) the antisense strand of the double stranded siRNA molecule and (3) the terminator sequence.

19. The method of claim 18, further comprising a second polymerase chain reaction amplification comprising:

(a) adding a double stranded nucleic acid comprising a mammalian promoter to an amplification reaction mixture, wherein the double stranded nucleic acid has a sense strand and an antisense strand and wherein each of the sense strand and antisense strand has a 5' end and a 3' end, wherein the mammalian promoter is capable of transcribing an RNA molecule in mammalian cells;

(b) adding a first oligonucleotide primer to the reaction mixture, wherein the first oligonucleotide primer is complementary to the 3' end of the antisense strand of the double stranded nucleic acid;

(c) adding a second oligonucleotide primer to the reaction mixture, wherein the second oligonucleotide primer is complementary to the 3' end of the sense strand of the double stranded nucleic acid and wherein the second oligonucleotide primer comprises a nucleotide sequence that is complementary to a nucleotide sequence that encodes (1) an sense sequence of the double stranded siRNA molecule and (2) a terminator sequence; and (d) amplifying the double stranded nucleic acid in a polymerase chain reaction amplification comprising (i) annealing the primers to the complementary strands of the double stranded nucleic acid, (ii) extending the annealed primers to produce extension products, (iii) denaturing the extension products and (iv) repeating the polymerase chain reaction amplification steps a sufficient number of times to produce a second amplified product comprising a second mammalian promoter-containing expression cassette, wherein the second mammalian promoter-containing expression cassette comprises (1) the mammalian promoter, (2) the sense strand of the double stranded siRNA molecule and (3) the terminator sequence.

20. The method of claim 19, further comprising the step of transfecting a mammalian cell in vitro with the first amplified mammalian promoter-containing expression cassette and with the second amplified mammalian promoter-containing expression cassette, wherein the sense strand of the double stranded siRNA molecule and the antisense strand of the double stranded siRNA molecule are expressed in the transfected cell, whereby a double stranded siRNA molecule is produced in the transfected cell.

* * * * *

UNITED STATES PATENT AND TRADEMARK OFFICE
CERTIFICATE OF CORRECTION

PATENT NO.       : 8,389,244 B2                                                   Page 1 of 1
APPLICATION NO.  : 10/630968
DATED            : March 5, 2013
INVENTOR(S)      : Rossi et al.

It is certified that error appears in the above-identified patent and that said Letters Patent is hereby corrected as shown below:

*In the Specification*

Col. 15 [SEQ ID NO 12]: "C<u>GGTGTTTCGTCCTTTCCACAAG</u>" should be
-- C<u>GGTGTTTCGTCCTTTCCACAAG</u> --

Col. 17 [SEQ ID NO 19]: "CGGAGACAGCGACGAAGAGC" should be
-- CGGAGACA<u>GCG</u>ACGAAGAGC --

Col. 17 [SEQ ID NO 19]: "GCTCTTCGTCGCTGTCCGC" should be
-- GCTCTTCGTCGCTGTCTCCGC --

Col. 18 [SEQ ID NO 28]: "GGTTAAGATCTAAAAAATTCAG" should be
-- CGGTTAAGATCTAAAAAATTCCAG --

Col. 18 [SEQ ID NO 32]: "C<u>GGTGTTTCGTCCTTTCCACAAG</u>" should be
-- C<u>GGTGTTTCGTCCTTTCCACAAG</u> --

Col. 19 [SEQ ID NO 34]:
"TCCCCCGGGACATGCATGCATGAAAAAAGCCTGTGCCTCTTCQA" should be
-- TCCCCCGGGACATGCATGCATGAAAAAAGCCTGTGCCTCTTCA --

Col. 19 [SEQ ID "NO 36]: "TTTCAATCTGA" should be -- TTTAATCTGA --

Signed and Sealed this
Tenth Day of June, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,389,244 B2
APPLICATION NO. : 10/630968
DATED : March 5, 2013
INVENTOR(S) : John J. Rossi et al.

It is certified that error appears in the above-identified patent and that said Letters Patent is hereby corrected as shown below:

In the Specification

Column 1, Lines 10-14:
"This invention was made with federal government support from the National Institutes of Health of the U.S. Department of Health and Human Services under Grant No. AI29329 to the City of Hope Cancer Center. The United States government may have certain rights in this invention."
Should be:
-- This invention was made with government support under AI029329 awarded by the National Institutes of Health. The government has certain rights in the invention. --

Signed and Sealed this
Twenty-eighth Day of May, 2024

Katherine Kelly Vidal
*Director of the United States Patent and Trademark Office*

SEQUENCE LISTING

```
<160> NUMBER OF SEQ ID NOS: 38

<210> SEQ ID NO 1
<211> LENGTH: 21
<212> TYPE: DNA
<213> ORGANISM: Artificial Sequence
<220> FEATURE:
<223> OTHER INFORMATION: chimeric nucleotide target sequence

<400> SEQUENCE: 1
gcctgtgcct cttcagctac c                                              21

<210> SEQ ID NO 2
<211> LENGTH: 40
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<222> LOCATION: (12)..(40)
<223> OTHER INFORMATION: homologous to the 5' end of the u6 promoter

<400> SEQUENCE: 2
atcgcagatc tggatccaag gtcgggcagg aagagggcct                          40

<210> SEQ ID NO 3
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: homologous to the 3' end of the u6 promoter

<400> SEQUENCE: 3
gtggaaagga cgaaacaccg                                                20

<210> SEQ ID NO 4
<211> LENGTH: 68
<212> TYPE: DNA
```

```
<213> ORGANISM: Human immunodeficiency virus
<220> FEATURE:
<221> NAME/KEY: misc_feature
<222> LOCATION: (18)..(38)
<223> OTHER INFORMATION: siRNA encoding sequence

<400> SEQUENCE: 4
cgaaaaggcc taaaaaggt agctgaagag gcacaggcgg tgtttcgtcc tttccacaag    60
atatataa                                                            68

<210> SEQ ID NO 5
<211> LENGTH: 68
<212> TYPE: DNA
<213> ORGANISM: Human immunodeficiency virus
<220> FEATURE:
<221> NAME/KEY: misc_feature
<222> LOCATION: (18)..(38)
<223> OTHER INFORMATION: siRNA encoding sequence

<400> SEQUENCE: 5
cgaaaaggcc taaaaagcc tgtgcctctt cagctaccgg tgtttcgtcc tttccacaag    60
atatataa                                                            68

<210> SEQ ID NO 6
<211> LENGTH: 58
<212> TYPE: DNA
<213> ORGANISM: Human immunodeficiency virus
<220> FEATURE:
<221> NAME/KEY: misc_feature
<222> LOCATION: (9)..(29)
<223> OTHER INFORMATION: siRNA encoding sequence

<400> SEQUENCE: 6
tacacaaagg tagctgaaga ggcacaggcg gtgtttcgtc ctttccacaa gatatata     58

<210> SEQ ID NO 7
<211> LENGTH: 49
<212> TYPE: DNA
<213> ORGANISM: Human immunodeficiency virus
<220> FEATURE:
<221> NAME/KEY: misc_feature
<222> LOCATION: (18)..(38)
<223> OTHER INFORMATION: siRNA encoding sequence

<400> SEQUENCE: 7
cgaaaaggcc taaaaagcc tgtgcctctt cagctaccct acacaaagg                49

<210> SEQ ID NO 8
<211> LENGTH: 36
<212> TYPE: DNA
<213> ORGANISM: Artificial Sequence
<220> FEATURE:
<223> OTHER INFORMATION: chimeric nucleotide construct
<220> FEATURE:
<221> NAME/KEY: misc_feature
<222> LOCATION: (17)..(36)
<223> OTHER INFORMATION: homologous to 5' end of the u6+1 promoter

<400> SEQUENCE: 8
ataagaatgc ggccgccccg gggatccaag gtcggg                             36

<210> SEQ ID NO 9
<211> LENGTH: 89
<212> TYPE: DNA
<213> ORGANISM: Artificial Sequence
<220> FEATURE:
<223> OTHER INFORMATION: chimeric nucleotide construct
<220> FEATURE:
```

```
<221> NAME/KEY: misc_feature
<222> LOCATION: (1)..(23)
<223> OTHER INFORMATION: 3' end of the U6+1 promoter
<220> FEATURE:
<221> NAME/KEY: misc_feature
<222> LOCATION: (24)..(44)
<223> OTHER INFORMATION: sequence coding for sense hairpin RNA
<220> FEATURE:
<221> NAME/KEY: misc_feature
<222> LOCATION: (45)..(53)
<223> OTHER INFORMATION: sequence coding for nucleotide loop
<220> FEATURE:
<221> NAME/KEY: misc_feature
<222> LOCATION: (54)..(74)
<223> OTHER INFORMATION: sequence coding for anti-sense hairpin RNA
<220> FEATURE:
<221> NAME/KEY: misc_feature
<222> LOCATION: (75)..(80)
<223> OTHER INFORMATION: sequence coding for termination signal
<220> FEATURE:
<221> NAME/KEY: misc_feature
<222> LOCATION: (81)..(86)
<223> OTHER INFORMATION: Bgl2 site

<400> SEQUENCE: 9
cttgtggaaa ggacgaaaca ccgcaacaca actgtttaat agtatttgtg tagtactatt    60
aaacagttgt gttgtttttt agatcttcc                                      89

<210> SEQ ID NO 10
<211> LENGTH: 89
<212> TYPE: DNA
<213> ORGANISM: Artificial Sequence
<220> FEATURE:
<223> OTHER INFORMATION: chimeric nucleotide construct
<220> FEATURE:
<221> NAME/KEY: misc_feature
<222> LOCATION: (4)..(9)
<223> OTHER INFORMATION: Bgl2 site
<220> FEATURE:
<221> NAME/KEY: misc_feature
<222> LOCATION: (10)..(15)
<223> OTHER INFORMATION: sequence coding for termination signal
<220> FEATURE:
<221> NAME/KEY: misc_feature
<222> LOCATION: (16)..(36)
<223> OTHER INFORMATION: sequence coding for anti-sense hairpin RNA
<220> FEATURE:
<221> NAME/KEY: misc_feature
<222> LOCATION: (37)..(45)
<223> OTHER INFORMATION: sequence coding for nucleotide loop
<220> FEATURE:
<221> NAME/KEY: misc_feature
<222> LOCATION: (46)..(66)
<223> OTHER INFORMATION: sequence coding for sense hairpin RNA
<220> FEATURE:
<221> NAME/KEY: misc_feature
<222> LOCATION: (67)..(89)
<223> OTHER INFORMATION: 3' end of the U6+1 promoter

<400> SEQUENCE: 10
ggaagatcta aaaacaaca caactgttta atagtactac acaaatacta ttaaacagtt    60
gtgttgcggt gtttcgtcct ttccacaag                                      89

<210> SEQ ID NO 11
<211> LENGTH: 89
<212> TYPE: DNA
<213> ORGANISM: Artificial Sequence
<220> FEATURE:
<223> OTHER INFORMATION: chimeric nucleotide construct
<220> FEATURE:
<221> NAME/KEY: misc_feature
<222> LOCATION: (1)..(23)
<223> OTHER INFORMATION: 3' end of the u6+1 promoter
<220> FEATURE:
```

```
<221> NAME/KEY: misc_feature
<222> LOCATION: (24)..(44)
<223> OTHER INFORMATION: sequence coding for sense hairpin RNA
<220> FEATURE:
<221> NAME/KEY: misc_feature
<222> LOCATION: (45)..(53)
<223> OTHER INFORMATION: sequence coding for nucleotide loop
<220> FEATURE:
<221> NAME/KEY: misc_feature
<222> LOCATION: (54)..(74)
<223> OTHER INFORMATION: sequence coding for anit-sense hairpin RNA loop
<220> FEATURE:
<221> NAME/KEY: misc_feature
<222> LOCATION: (75)..(80)
<223> OTHER INFORMATION: sequence coding for termination signal
<220> FEATURE:
<221> NAME/KEY: misc_feature
<222> LOCATION: (81)..(86)
<223> OTHER INFORMATION: Bgl2 site

<400> SEQUENCE: 11
cttgtggaaa ggacgaaaca ccgcacaatc acactcccat gcagtttgtg tagctgcatg      60
ggagtgtgat tgtgtttttt agatcttcc                                        89

<210> SEQ ID NO 12
<211> LENGTH: 89
<212> TYPE: DNA
<213> ORGANISM: Artificial Sequence
<220> FEATURE:
<223> OTHER INFORMATION: chimeric nucleotide construct
<220> FEATURE:
<221> NAME/KEY: misc_feature
<222> LOCATION: (4)..(9)
<223> OTHER INFORMATION: Bgl2 site
<220> FEATURE:
<221> NAME/KEY: misc_feature
<222> LOCATION: (10)..(15)
<223> OTHER INFORMATION: sequence coding for termination signal
<220> FEATURE:
<221> NAME/KEY: misc_feature
<222> LOCATION: (16)..(36)
<223> OTHER INFORMATION: sequence coding for anti-sense hairpin RNA
<220> FEATURE:
<221> NAME/KEY: misc_feature
<222> LOCATION: (37)..(45)
<223> OTHER INFORMATION: sequence coding for nucleotide loop
<220> FEATURE:
<221> NAME/KEY: misc_feature
<222> LOCATION: (46)..(66)
<223> OTHER INFORMATION: sequence coding for sense hairpin RNA
<220> FEATURE:
<221> NAME/KEY: misc_feature
<222> LOCATION: (67)..(89)
<223> OTHER INFORMATION: 3' end of the u6+1 promoter

<400> SEQUENCE: 12
ggaagatcta aaaacacaa tcacactccc atgcagctac acaaactgca tgggagtgtg        60
attgtgcggt gtttcgtcct ttccacaag                                        89

<210> SEQ ID NO 13
<211> LENGTH: 88
<212> TYPE: DNA
<213> ORGANISM: Artificial Sequence
<220> FEATURE:
<223> OTHER INFORMATION: chimeric nucleotide construct
<220> FEATURE:
<221> NAME/KEY: misc_feature
<222> LOCATION: (1)..(23)
<223> OTHER INFORMATION: 3' end of the U6+1 promoter
<220> FEATURE:
<221> NAME/KEY: misc_feature
<222> LOCATION: (24)..(43)
<223> OTHER INFORMATION: sequence coding for sense hairpin RNA
<220> FEATURE:
```

```
<221> NAME/KEY: misc_feature
<222> LOCATION: (44)..(52)
<223> OTHER INFORMATION: sequence coding for nucleotide loop
<220> FEATURE:
<221> NAME/KEY: misc_feature
<222> LOCATION: (53)..(73)
<223> OTHER INFORMATION: sequence coding for anti-sense hairpin RNA
<220> FEATURE:
<221> NAME/KEY: misc_feature
<222> LOCATION: (74)..(79)
<223> OTHER INFORMATION: sequence coding for termination signal
<220> FEATURE:
<221> NAME/KEY: misc_feature
<222> LOCATION: (80)..(85)
<223> OTHER INFORMATION: Bgl2 site

<400> SEQUENCE: 13
cttgtggaaa ggacgaaaca ccggaggagg cgatatgagg gactttgtgt aggtccctca    60
tatcgcctcc tccttttta gatcttcc                                        88

<210> SEQ ID NO 14
<211> LENGTH: 88
<212> TYPE: DNA
<213> ORGANISM: Artificial Sequence
<220> FEATURE:
<223> OTHER INFORMATION: chimeric oligonucleotide construct
<220> FEATURE:
<221> NAME/KEY: misc_feature
<222> LOCATION: (4)..(9)
<223> OTHER INFORMATION: Bgl2 site
<220> FEATURE:
<221> NAME/KEY: misc_feature
<222> LOCATION: (10)..(15)
<223> OTHER INFORMATION: sequence coding for termination signal
<220> FEATURE:
<221> NAME/KEY: misc_feature
<222> LOCATION: (16)..(36)
<223> OTHER INFORMATION: sequence coding for anti-sense hairpin RNA
<220> FEATURE:
<221> NAME/KEY: misc_feature
<222> LOCATION: (37)..(45)
<223> OTHER INFORMATION: sequence coding for nucleotide loop
<220> FEATURE:
<221> NAME/KEY: misc_feature
<222> LOCATION: (46)..(65)
<223> OTHER INFORMATION: sequence coding for sense hairpin RNA
<220> FEATURE:
<221> NAME/KEY: misc_feature
<222> LOCATION: (66)..(88)
<223> OTHER INFORMATION: 3' end of the u6+1 promoter

<400> SEQUENCE: 14
ggaagatcta aaaaggagg aggcgatatg agggacctac acaaagtccc tcatatcgcc     60
tcctccggtg tttcgtcctt tccacaag                                       88

<210> SEQ ID NO 15
<211> LENGTH: 89
<212> TYPE: DNA
<213> ORGANISM: Artificial Sequence
<220> FEATURE:
<223> OTHER INFORMATION: chimeric oligonucleotide construct
<220> FEATURE:
<221> NAME/KEY: misc_feature
<222> LOCATION: (1)..(23)
<223> OTHER INFORMATION: 3' end of the u6+1 promoter
<220> FEATURE:
<221> NAME/KEY: misc_feature
<222> LOCATION: (24)..(44)
<223> OTHER INFORMATION: sequence coding for sense hairpin RNA
<220> FEATURE:
<221> NAME/KEY: misc_feature
<222> LOCATION: (45)..(53)
<223> OTHER INFORMATION: sequence coding for nucleotide loop
<220> FEATURE:
```

```
<221> NAME/KEY: misc_feature
<222> LOCATION: (54)..(74)
<223> OTHER INFORMATION: sequence coding for anti-sense hairpin RNA
<220> FEATURE:
<221> NAME/KEY: misc_feature
<222> LOCATION: (75)..(80)
<223> OTHER INFORMATION: sequence coding for termination signal
<220> FEATURE:
<221> NAME/KEY: misc_feature
<222> LOCATION: (81)..(86)
<223> OTHER INFORMATION: Bgl2 site

<400> SEQUENCE: 15
cttgtggaaa ggacgaaaca ccgtgtctga tatagtgcag cagctttgtg taggctgctg      60
cactatatca gacatttttt agatcttcc                                        89

<210> SEQ ID NO 16
<211> LENGTH: 89
<212> TYPE: DNA
<213> ORGANISM: Artificial Sequence
<220> FEATURE:
<223> OTHER INFORMATION: chimeric nucleotide construct
<220> FEATURE:
<221> NAME/KEY: misc_feature
<222> LOCATION: (4)..(9)
<223> OTHER INFORMATION: Bgl2 site
<220> FEATURE:
<221> NAME/KEY: misc_feature
<222> LOCATION: (10)..(15)
<223> OTHER INFORMATION: sequence coding for termination signal
<220> FEATURE:
<221> NAME/KEY: misc_feature
<222> LOCATION: (16)..(36)
<223> OTHER INFORMATION: sequence coding for anti-sense hairpin RNA
<220> FEATURE:
<221> NAME/KEY: misc_feature
<222> LOCATION: (37)..(45)
<223> OTHER INFORMATION: sequence coding for nucleotide loop
<220> FEATURE:
<221> NAME/KEY: misc_feature
<222> LOCATION: (46)..(67)
<223> OTHER INFORMATION: sequence coding for sense hairpin loop
<220> FEATURE:
<221> NAME/KEY: misc_feature
<222> LOCATION: (68)..(89)
<223> OTHER INFORMATION: 3 'end of the u6+1 promoter

<400> SEQUENCE: 16
ggaagatcta aaaaatgtct gatatagtgc agcagcctac acaaagctgc tgcactatat      60
cagacacggt gtttcgtcct ttccacaag                                        89

<210> SEQ ID NO 17
<211> LENGTH: 89
<212> TYPE: DNA
<213> ORGANISM: Artificial Sequence
<220> FEATURE:
<223> OTHER INFORMATION: chimeric nucleotide construct
<220> FEATURE:
<221> NAME/KEY: misc_feature
<222> LOCATION: (1)..(23)
<223> OTHER INFORMATION: 3' end of the u6+1 promoter
<220> FEATURE:
<221> NAME/KEY: misc_feature
<222> LOCATION: (24)..(44)
<223> OTHER INFORMATION: sequence coding for sense hairpin RNA
<220> FEATURE:
<221> NAME/KEY: misc_feature
<222> LOCATION: (45)..(53)
<223> OTHER INFORMATION: sequence coding for nucleotide loop
<220> FEATURE:
<221> NAME/KEY: misc_feature
<222> LOCATION: (54)..(74)
<223> OTHER INFORMATION: sequence coding for anti-sense hairpin RNA
<220> FEATURE:
```

```
<221> NAME/KEY: misc_feature
<222> LOCATION: (75)..(80)
<223> OTHER INFORMATION: sequence coding for termination signal
<220> FEATURE:
<221> NAME/KEY: misc_feature
<222> LOCATION: (81)..(86)
<223> OTHER INFORMATION: Bgl2 site

<400> SEQUENCE: 17
cttgtggaaa ggacgaaaca ccgtctgttg caactcacag tctgtttgtg tagcagactg      60
tgagttgcaa cagattttt agatcttcc                                        89

<210> SEQ ID NO 18
<211> LENGTH: 89
<212> TYPE: DNA
<213> ORGANISM: Artificial Sequence
<220> FEATURE:
<223> OTHER INFORMATION: chimeric oligonucleotide construct
<220> FEATURE:
<221> NAME/KEY: misc_feature
<222> LOCATION: (4)..(9)
<223> OTHER INFORMATION: Bgl2 site
<220> FEATURE:
<221> NAME/KEY: misc_feature
<222> LOCATION: (10)..(15)
<223> OTHER INFORMATION: sequence coding for termination signal
<220> FEATURE:
<221> NAME/KEY: misc_feature
<222> LOCATION: (16)..(36)
<223> OTHER INFORMATION: sequence coding for anti-sense hairpin RNA
<220> FEATURE:
<221> NAME/KEY: misc_feature
<222> LOCATION: (37)..(45)
<223> OTHER INFORMATION: sequence coding for nucleotide loop
<220> FEATURE:
<221> NAME/KEY: misc_feature
<222> LOCATION: (46)..(66)
<223> OTHER INFORMATION: sequence coding for sense hairpin RNA
<220> FEATURE:
<221> NAME/KEY: misc_feature
<222> LOCATION: (67)..(89)
<223> OTHER INFORMATION: 3' end of the u6+1 promoter

<400> SEQUENCE: 18
ggaagatcta aaaaatctgt tgcaactcac agtctgctac acaaacagac tgtgagttgc      60
aacagacggt gtttcgtcct ttccacaag                                       89

<210> SEQ ID NO 19
<211> LENGTH: 88
<212> TYPE: DNA
<213> ORGANISM: Artificial Sequence
<220> FEATURE:
<223> OTHER INFORMATION: chimeric nucleotide construct
<220> FEATURE:
<221> NAME/KEY: misc_feature
<222> LOCATION: (1)..(23)
<223> OTHER INFORMATION: 3' end of the u6+1 promoter
<220> FEATURE:
<221> NAME/KEY: misc_feature
<222> LOCATION: (24)..(43)
<223> OTHER INFORMATION: sequence coding for sense hairpin RNA
<220> FEATURE:
<221> NAME/KEY: misc_feature
<222> LOCATION: (32)..(34)
<223> OTHER INFORMATION: site of mismatched nucleotides in negative
     control
<220> FEATURE:
<221> NAME/KEY: misc_feature
<222> LOCATION: (44)..(52)
<223> OTHER INFORMATION: sequence coding for nucleotide loop
<220> FEATURE:
<221> NAME/KEY: misc_feature
<222> LOCATION: (53)..(73)
<223> OTHER INFORMATION: sequence coding for anti-sense hairpin RNA
```

```
<220> FEATURE:
<221> NAME/KEY: misc_feature
<222> LOCATION: (62)..(64)
<223> OTHER INFORMATION: site of mismatched nucleotides in negative
      control
<220> FEATURE:
<221> NAME/KEY: misc_feature
<222> LOCATION: (74)..(79)
<223> OTHER INFORMATION: sequence coding for termination signal
<220> FEATURE:
<221> NAME/KEY: misc_feature
<222> LOCATION: (80)..(85)
<223> OTHER INFORMATION: Bg12 site

<400> SEQUENCE: 19
cttgtggaaa ggacgaaaca ccgcggagac agcgacgaag agctttgtgt aggctcttcg      60
tcgctgtctc cgcttttta gatcttcc                                         88

<210> SEQ ID NO 20
<211> LENGTH: 88
<212> TYPE: DNA
<213> ORGANISM: Artificial Sequence
<220> FEATURE:
<223> OTHER INFORMATION: chimeric nucleotide construct
<220> FEATURE:
<221> NAME/KEY: misc_feature
<222> LOCATION: (4)..(9)
<223> OTHER INFORMATION: Bg12 site
<220> FEATURE:
<221> NAME/KEY: misc_feature
<222> LOCATION: (10)..(15)
<223> OTHER INFORMATION: sequence coding for termination signal
<220> FEATURE:
<221> NAME/KEY: misc_feature
<222> LOCATION: (16)..(36)
<223> OTHER INFORMATION: sequence coding for anti-sense hairpin RNA
<220> FEATURE:
<221> NAME/KEY: misc_feature
<222> LOCATION: (37)..(45)
<223> OTHER INFORMATION: sequence coding for nucleotide loop
<220> FEATURE:
<221> NAME/KEY: misc_feature
<222> LOCATION: (46)..(65)
<223> OTHER INFORMATION: sequence coding for sense hairpin RNA
<220> FEATURE:
<221> NAME/KEY: misc_feature
<222> LOCATION: (66)..(88)
<223> OTHER INFORMATION: 3' end of the u6+1 promoter

<400> SEQUENCE: 20
ggaagatcta aaaaagcgga gacagcgacg aagagcctac acaaagctct tcgtcgctgt      60
ctccgcggtg tttcgtcctt tccacaag                                        88

<210> SEQ ID NO 21
<211> LENGTH: 88
<212> TYPE: DNA
<213> ORGANISM: Artificial Sequence
<220> FEATURE:
<223> OTHER INFORMATION: chimeric nucleotide construct
<220> FEATURE:
<221> NAME/KEY: misc_feature
<222> LOCATION: (1)..(23)
<223> OTHER INFORMATION: 3' end of the u6+1 promoter
<220> FEATURE:
<221> NAME/KEY: misc_feature
<222> LOCATION: (24)..(43)
<223> OTHER INFORMATION: sequence coding for sense hairpin RNA
<220> FEATURE:
<221> NAME/KEY: misc_feature
<222> LOCATION: (32)..(34)
<223> OTHER INFORMATION: mismatched nucleotides
<220> FEATURE:
<221> NAME/KEY: misc_feature
<222> LOCATION: (44)..(52)
```

```
<223> OTHER INFORMATION: sequence coding for nucleotide loop
<220> FEATURE:
<221> NAME/KEY: misc_feature
<222> LOCATION: (53)..(73)
<223> OTHER INFORMATION: sequence coding for anti-sense hairpin RNA
<220> FEATURE:
<221> NAME/KEY: misc_feature
<222> LOCATION: (62)..(64)
<223> OTHER INFORMATION: mismatched nucleotides
<220> FEATURE:
<221> NAME/KEY: misc_feature
<222> LOCATION: (74)..(79)
<223> OTHER INFORMATION: sequence coding for termination signal
<220> FEATURE:
<221> NAME/KEY: misc_feature
<222> LOCATION: (80)..(85)
<223> OTHER INFORMATION: Bg12 site

<400> SEQUENCE: 21
cttgtggaaa ggacgaaaca ccgcggagac atatacgaag agctttgtgt aggctcttcg        60
tatatgtctc cgctttttta gatcttcc                                          88

<210> SEQ ID NO 22
<211> LENGTH: 88
<212> TYPE: DNA
<213> ORGANISM: Artificial Sequence
<220> FEATURE:
<223> OTHER INFORMATION: chimeric oligonucleotide construct
<220> FEATURE:
<221> NAME/KEY: misc_feature
<222> LOCATION: (4)..(9)
<223> OTHER INFORMATION: Bg12 site
<220> FEATURE:
<221> NAME/KEY: misc_feature
<222> LOCATION: (10)..(15)
<223> OTHER INFORMATION: sequence coding for termination signal
<220> FEATURE:
<221> NAME/KEY: misc_feature
<222> LOCATION: (16)..(36)
<223> OTHER INFORMATION: sequence coding for anti-sense hairpin RNA
<220> FEATURE:
<221> NAME/KEY: misc_feature
<222> LOCATION: (25)..(27)
<223> OTHER INFORMATION: mismatched nucleotides
<220> FEATURE:
<221> NAME/KEY: misc_feature
<222> LOCATION: (37)..(45)
<223> OTHER INFORMATION: sequence coding for nucleotide loop
<220> FEATURE:
<221> NAME/KEY: misc_feature
<222> LOCATION: (46)..(65)
<223> OTHER INFORMATION: sequence coding for sense hairpin RNA
<220> FEATURE:
<221> NAME/KEY: misc_feature
<222> LOCATION: (55)..(57)
<223> OTHER INFORMATION: mismatched nucleotides
<220> FEATURE:
<221> NAME/KEY: misc_feature
<222> LOCATION: (66)..(88)
<223> OTHER INFORMATION: 3' end of the u6+1 promoter

<400> SEQUENCE: 22
ggaagatcta aaaaagcgga gacatatacg aagagcctac acaaagctct tcgtatatgt        60
ctccgcggtg tttcgtcctt tccacaag                                          88

<210> SEQ ID NO 23
<211> LENGTH: 88
<212> TYPE: DNA
<213> ORGANISM: Artificial Sequence
<220> FEATURE:
<223> OTHER INFORMATION: chimeric oligonucleotide construct
<220> FEATURE:
<221> NAME/KEY: misc_feature
<222> LOCATION: (1)..(23)
```

```
<223> OTHER INFORMATION: 3' end of the u6+1 promoter
<220> FEATURE:
<221> NAME/KEY: misc_feature
<222> LOCATION: (24)..(43)
<223> OTHER INFORMATION: sequence coding for sense hairpin RNA
<220> FEATURE:
<221> NAME/KEY: misc_feature
<222> LOCATION: (44)..(52)
<223> OTHER INFORMATION: sequence coding for nucleotide loop
<220> FEATURE:
<221> NAME/KEY: misc_feature
<222> LOCATION: (49)..(50)
<223> OTHER INFORMATION: changed loop nucleotides
<220> FEATURE:
<221> NAME/KEY: misc_feature
<222> LOCATION: (53)..(73)
<223> OTHER INFORMATION: sequence coding for anti-sense hairpin RNA
<220> FEATURE:
<221> NAME/KEY: misc_feature
<222> LOCATION: (74)..(79)
<223> OTHER INFORMATION: sequence coding for termination signal
<220> FEATURE:
<221> NAME/KEY: misc_feature
<222> LOCATION: (80)..(85)
<223> OTHER INFORMATION: Bgl2 site

<400> SEQUENCE: 23
cttgtggaaa ggacgaaaca ccgcggagac agcgacgaag agctttgtac aggctcttcg      60
tcgctgtctc cgcttttta gatcttcc                                          88

<210> SEQ ID NO 24
<211> LENGTH: 88
<212> TYPE: DNA
<213> ORGANISM: Artificial Sequence
<220> FEATURE:
<223> OTHER INFORMATION: chimeric nucleotide construct
<220> FEATURE:
<221> NAME/KEY: misc_feature
<222> LOCATION: (4)..(9)
<223> OTHER INFORMATION: Bgl2 site
<220> FEATURE:
<221> NAME/KEY: misc_feature
<222> LOCATION: (10)..(15)
<223> OTHER INFORMATION: sequence coding for termination signal
<220> FEATURE:
<221> NAME/KEY: misc_feature
<222> LOCATION: (16)..(36)
<223> OTHER INFORMATION: sequence coding for anti-sense hairpin RNA
<220> FEATURE:
<221> NAME/KEY: misc_feature
<222> LOCATION: (37)..(45)
<223> OTHER INFORMATION: sequence coding for nucleotide loop
<220> FEATURE:
<221> NAME/KEY: misc_feature
<222> LOCATION: (46)..(65)
<223> OTHER INFORMATION: sequence coding for sense hairpin RNA
<220> FEATURE:
<221> NAME/KEY: misc_feature
<222> LOCATION: (66)..(88)
<223> OTHER INFORMATION: 3' end of the u6+1 promoter

<400> SEQUENCE: 24
ggaagatcta aaaaagcgga gacagcgacg aagagcctgt acaagctct tcgtcgctgt       60 ctccgcggtg tttcgtcctt tccacaag                                         88

<210> SEQ ID NO 25
<211> LENGTH: 14
<212> TYPE: DNA
<213> ORGANISM: Human immunodeficiency virus

<400> SEQUENCE: 25
ttccagtcag acct                                                        14
```

```
<210> SEQ ID NO 26
<211> LENGTH: 27
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (3)..(23)

<400> SEQUENCE: 26
ttttccagtc acacctcagg taccttt                                              27

<210> SEQ ID NO 27
<211> LENGTH: 91
<212> TYPE: DNA
<213> ORGANISM: Artificial Sequence
<220> FEATURE:
<223> OTHER INFORMATION: chimeric nucleotide construct
<220> FEATURE:
<221> NAME/KEY: misc_feature
<222> LOCATION: (1)..(23)
<223> OTHER INFORMATION: 3' end of the u6+1 promoter
<220> FEATURE:
<221> NAME/KEY: misc_feature
<222> LOCATION: (24)..(44)
<223> OTHER INFORMATION: sequence coding for sense hairpin RNA
<220> FEATURE:
<221> NAME/KEY: misc_feature
<222> LOCATION: (45)..(53)
<223> OTHER INFORMATION: sequence coding for nucleotide loop
<220> FEATURE:
<221> NAME/KEY: misc_feature
<222> LOCATION: (54)..(74)
<223> OTHER INFORMATION: sequence coding for anti-sense hairpin RNA
<220> FEATURE:
<221> NAME/KEY: misc_feature
<222> LOCATION: (75)..(80)
<223> OTHER INFORMATION: sequence coding for termination signal
<220> FEATURE:
<221> NAME/KEY: misc_feature
<222> LOCATION: (81)..(86)
<223> OTHER INFORMATION: Bgl2 site

<400> SEQUENCE: 27
cttgtggaaa ggacgaaaca ccgttccagt cacacctcag gtactttgtg taggtacctg          60
aggtgtgact ggaattttt agatcttaac c                                         91

<210> SEQ ID NO 28
<211> LENGTH: 91
<212> TYPE: DNA
<213> ORGANISM: Artificial Sequence
<220> FEATURE:
<223> OTHER INFORMATION: chimeric nucleotide construct
<220> FEATURE:
<221> NAME/KEY: misc_feature
<222> LOCATION: (6)..(11)
<223> OTHER INFORMATION: Bgl2 site
<220> FEATURE:
<221> NAME/KEY: misc_feature
<222> LOCATION: (12)..(17)
<223> OTHER INFORMATION: sequence coding for termination signal
<220> FEATURE:
<221> NAME/KEY: misc_feature
<222> LOCATION: (18)..(38)
<223> OTHER INFORMATION: sequence coding for anti-sense hairpin RNA
<220> FEATURE:
<221> NAME/KEY: misc_feature
<222> LOCATION: (39)..(47)
<223> OTHER INFORMATION: sequence coding for nucleotide loop
<220> FEATURE:
<221> NAME/KEY: misc_feature
<222> LOCATION: (48)..(68)
<223> OTHER INFORMATION: sequence coding for sense hairpin RNA
```

```
<220> FEATURE:
<221> NAME/KEY: misc_feature
<222> LOCATION: (69)..(91)
<223> OTHER INFORMATION: 3' end of the u6+1 promoter

<400> SEQUENCE: 28
ggttaagatc taaaaaattc cagtcacacc tcaggtacct acacaaagta cctgaggtgt    60
gactggaacg gtgtttcgtc ctttccacaa g                                  91

<210> SEQ ID NO 29
<211> LENGTH: 19
<212> TYPE: DNA
<213> ORGANISM: Artificial Sequence
<220> FEATURE:
<223> OTHER INFORMATION: oligonucleotide

<400> SEQUENCE: 29
gctctattag atacaggag                                                19

<210> SEQ ID NO 30
<211> LENGTH: 27
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (4)..(24)

<400> SEQUENCE: 30
gaagctctat tagatacagg agcagat                                       27

<210> SEQ ID NO 31
<211> LENGTH: 90
<212> TYPE: DNA
<213> ORGANISM: Artificial Sequence
<220> FEATURE:
<223> OTHER INFORMATION: chimeric nucleotide construct
<220> FEATURE:
<221> NAME/KEY: misc_feature
<222> LOCATION: (1)..(23)
<223> OTHER INFORMATION: 3' end of the u6+ promoter
<220> FEATURE:
<221> NAME/KEY: misc_feature
<222> LOCATION: (24)..(43)
<223> OTHER INFORMATION: sequence coding for sense hairpin RNA
<220> FEATURE:
<221> NAME/KEY: misc_feature
<222> LOCATION: (44)..(52)
<223> OTHER INFORMATION: sequence coding for nucleotide loop
<220> FEATURE:
<221> NAME/KEY: misc_feature
<222> LOCATION: (53)..(73)
<223> OTHER INFORMATION: sequence coding for anti-sense hairpin RNA
<220> FEATURE:
<221> NAME/KEY: misc_feature
<222> LOCATION: (74)..(79)
<223> OTHER INFORMATION: sequence coding for termination signal
<220> FEATURE:
<221> NAME/KEY: misc_feature
<222> LOCATION: (80)..(85)
<223> OTHER INFORMATION: Bgl2 site

<400> SEQUENCE: 31
cttgtggaaa ggacgaaaca ccgctctatt agatacagga gcatttgtgt agtgctcctg    60
tatctaatag agcttttta gatcttaacc                                     90

<210> SEQ ID NO 32
<211> LENGTH: 90
<212> TYPE: DNA
```

```
<213> ORGANISM: Artificial Sequence
<220> FEATURE:
<223> OTHER INFORMATION: chimeric nucleotide construct
<220> FEATURE:
<221> NAME/KEY: misc_feature
<222> LOCATION: (6)..(11)
<223> OTHER INFORMATION: Bg12 site
<220> FEATURE:
<221> NAME/KEY: misc_feature
<222> LOCATION: (12)..(17)
<223> OTHER INFORMATION: sequence coding for termination signal
<220> FEATURE:
<221> NAME/KEY: misc_feature
<222> LOCATION: (18)..(38)
<223> OTHER INFORMATION: sequence coding for anti-sense hairpin RNA
<220> FEATURE:
<221> NAME/KEY: misc_feature
<222> LOCATION: (39)..(47)
<223> OTHER INFORMATION: sequence coding for nucleotide loop
<220> FEATURE:
<221> NAME/KEY: misc_feature
<222> LOCATION: (48)..(67)
<223> OTHER INFORMATION: sequence coding for sense hairpin RNA
<220> FEATURE:
<221> NAME/KEY: misc_feature
<222> LOCATION: (68)..(90)
<223> OTHER INFORMATION: 3' end of the u6+1 promoter

<400> SEQUENCE: 32
ggttaagatc taaaaaagct ctattagata caggagcact acacaaatgc tcctgtatct      60
aatagagcgg tgtttcgtcc tttccacaag                                      90

<210> SEQ ID NO 33
<211> LENGTH: 100
<212> TYPE: DNA
<213> ORGANISM: Artificial Sequence
<220> FEATURE:
<223> OTHER INFORMATION: chimeric nucleotide construct
<220> FEATURE:
<221> NAME/KEY: misc_feature
<222> LOCATION: (1)..(23)
<223> OTHER INFORMATION: 3' end of the u6+1 promoter
<220> FEATURE:
<221> NAME/KEY: misc_feature
<222> LOCATION: (24)..(43)
<223> OTHER INFORMATION: sequence coding for sense hairpin RNA
<220> FEATURE:
<221> NAME/KEY: misc_feature
<222> LOCATION: (44)..(51)
<223> OTHER INFORMATION: sequence coding for nucleotide loop
<220> FEATURE:
<221> NAME/KEY: misc_feature
<222> LOCATION: (52)..(72)
<223> OTHER INFORMATION: sequence coding for anti-sense hairpin RNA
<220> FEATURE:
<221> NAME/KEY: misc_feature
<222> LOCATION: (73)..(78)
<223> OTHER INFORMATION: sequence coding for termination signal
<220> FEATURE:
<221> NAME/KEY: misc_feature
<222> LOCATION: (80)..(97)

<400> SEQUENCE: 33
cttgtggaaa ggacgaaaca ccgcctgtgc ctcttcagct accgaagctt gggtagctga      60
agaggcacag gctttttca tgcatgcatg tcccggggga                            100

<210> SEQ ID NO 34
<211> LENGTH: 98
<212> TYPE: DNA
<213> ORGANISM: Artificial Sequence
<220> FEATURE:
<223> OTHER INFORMATION: chimeric nucleotide construct
<220> FEATURE:
<221> NAME/KEY: misc_feature
```

<222> LOCATION: (1)..(21)
<223> OTHER INFORMATION: 3' end of the u6+1 promoter
<220> FEATURE:
<221> NAME/KEY: misc_feature
<222> LOCATION: (22)..(41)
<223> OTHER INFORMATION: sequence coding for sense hairpin RNA
<220> FEATURE:
<221> NAME/KEY: misc_feature
<222> LOCATION: (42)..(49)
<223> OTHER INFORMATION: sequence coding for nucleotide loop
<220> FEATURE:
<221> NAME/KEY: misc_feature
<222> LOCATION: (50)..(70)
<223> OTHER INFORMATION: sequence coding for anti-sense hairpin RNA
<220> FEATURE:
<221> NAME/KEY: misc_feature
<222> LOCATION: (71)..(76)
<223> OTHER INFORMATION: sequence coding for termination signal
<220> FEATURE:
<221> NAME/KEY: misc_feature
<222> LOCATION: (78)..(95)

<400> SEQUENCE: 34
acacctttcc tgctttgtgg cggacacgga gaagtcgatg gcttcgaacc catcgacttc    60
tccgtgtccg aaaaaagtac gtacgtacag ggcccct                              98

<210> SEQ ID NO 35
<211> LENGTH: 29
<212> TYPE: DNA
<213> ORGANISM: Artificial Sequence
<220> FEATURE:
<223> OTHER INFORMATION: primer

<400> SEQUENCE: 35
acgcgtcgac gcccggatag ctcggtcgg                                       29

<210> SEQ ID NO 36
<211> LENGTH: 82
<212> TYPE: DNA
<213> ORGANISM: Artificial Sequence
<220> FEATURE:
<223> OTHER INFORMATION: chimeric nucleotide construct
<220> FEATURE:
<221> NAME/KEY: misc_feature
<222> LOCATION: (20)..(63)
<223> OTHER INFORMATION: n = A in case of wild-type, and G in case of
      SELEX 2144
<220> FEATURE:
<221> NAME/KEY: misc_feature
<222> LOCATION: (76)..(76)
<223> OTHER INFORMATION: n = G in case of wild-type, and T in case of
      SELEX 2144
<220> FEATURE:
<221> NAME/KEY: misc_feature
<222> LOCATION: (79)..(79)
<223> OTHER INFORMATION: n = A in case of wild-type, and G in case of
      SELEX 2144

<400> SEQUENCE: 36
gtcgacgccc ggatagctcn gtcggtngag catcagactt ttaatctgag ggtccagggt    60
tcnagtccct gttcgngcnc ca                                              82

<210> SEQ ID NO 37
<211> LENGTH: 90
<212> TYPE: DNA
<213> ORGANISM: Artificial Sequence
<220> FEATURE:
<223> OTHER INFORMATION: chimeric nucleotide construct
<220> FEATURE:
<221> NAME/KEY: misc_feature
<222> LOCATION: (1)..(24)
<223> OTHER INFORMATION: 3' end of SELEX 2144 tRNA sequence

```
<220> FEATURE:
<221> NAME/KEY: misc_feature
<222> LOCATION: (25)..(45)
<223> OTHER INFORMATION: sequence coding for sense hairpin RNA
<220> FEATURE:
<221> NAME/KEY: misc_feature
<222> LOCATION: (46)..(54)
<223> OTHER INFORMATION: sequence coding for nucleotide loop
<220> FEATURE:
<221> NAME/KEY: misc_feature
<222> LOCATION: (55)..(75)
<223> OTHER INFORMATION: sequence coding for anti-sense hairpin RNA
<220> FEATURE:
<221> NAME/KEY: misc_feature
<222> LOCATION: (76)..(81)
<223> OTHER INFORMATION: sequence coding for termination signal
<220> FEATURE:
<221> NAME/KEY: misc_feature
<222> LOCATION: (82)..(87)
<223> OTHER INFORMATION: Bgl2 site

<400> SEQUENCE: 37
gttcgagtcc ctgttcgtgc accagcggag acagcgacga agagctttgt gtaggctctt    60
cgtcgctgtc tccgcttttt tagatcttcc                                     90

<210> SEQ ID NO 38
<211> LENGTH: 90
<212> TYPE: DNA
<213> ORGANISM: Artificial Sequence
<220> FEATURE:
<223> OTHER INFORMATION: chimeric nucleotide construct
<220> FEATURE:
<221> NAME/KEY: misc_feature
<222> LOCATION: (4)..(9)
<223> OTHER INFORMATION: Bgl2 site
<220> FEATURE:
<221> NAME/KEY: misc_feature
<222> LOCATION: (10)..(15)
<223> OTHER INFORMATION: sequence coding for termination signal
<220> FEATURE:
<221> NAME/KEY: misc_feature
<222> LOCATION: (16)..(36)
<223> OTHER INFORMATION: sequence coding for anti-sense hairpin RNA
<220> FEATURE:
<221> NAME/KEY: misc_feature
<222> LOCATION: (37)..(45)
<223> OTHER INFORMATION: sequence coding for nucleotide loop
<220> FEATURE:
<221> NAME/KEY: misc_feature
<222> LOCATION: (46)..(66)
<223> OTHER INFORMATION: sequence coding for sense hairpin RNA
<220> FEATURE:
<221> NAME/KEY: misc_feature
<222> LOCATION: (67)..(90)
<223> OTHER INFORMATION: 3' end of the u6+1 promoter

<400> SEQUENCE: 38
ggaagatcta aaaaagcgga gacagcgacg aagagcctac acaaagctct tcgtcgctgt    60
ctccgcgctc agggacaagc acgtggtaac                                     90
```